US012806190B2

(12) United States Patent
Monga et al.

(10) Patent No.: US 12,806,190 B2
(45) Date of Patent: Nov. 24, 2026

(54) FGFR TYROSINE KINASE INHIBITORS FOR THE TREATMENT OF HIGH-RISK NON-MUSCLE INVASIVE BLADDER CANCER

(71) Applicant: Janssen Pharmaceutica NV, Beerse (BE)

(72) Inventors: Manish Monga, Raritan, NJ (US); Mahadi Ali Baig, Raritan, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 1098 days.

(21) Appl. No.: 17/904,139

(22) PCT Filed: Feb. 11, 2021

(86) PCT No.: PCT/EP2021/053385
§ 371 (c)(1),
(2) Date: Aug. 12, 2022

(87) PCT Pub. No.: WO2021/160764
PCT Pub. Date: Aug. 19, 2021

(65) Prior Publication Data
US 2023/0110113 A1 Apr. 13, 2023

Related U.S. Application Data

(60) Provisional application No. 63/118,475, filed on Nov. 25, 2020, provisional application No. 63/018,914, (Continued)

(51) Int. Cl.

| | |
|---|---|
| ***A61K 31/498*** | (2006.01) |
| ***A61P 13/10*** | (2006.01) |
| ***A61P 35/00*** | (2006.01) |

(52) U.S. Cl.
CPC ............ *A61K 31/498* (2013.01); *A61P 13/10* (2018.01); *A61P 35/00* (2018.01)

(58) Field of Classification Search
CPC ........ A61K 31/498; A61P 13/10; A61P 35/00; A61P 35/04
See application file for complete search history.

(56) References Cited

U.S. PATENT DOCUMENTS

| | | | |
|---|---|---|---|
| 4,666,828 | A | 5/1987 | Gusella |
| 4,683,202 | A | 7/1987 | Mullis |

(Continued)

FOREIGN PATENT DOCUMENTS

| | | | |
|---|---|---|---|
| CN | 107889462 | A | 4/2018 |
| CN | 108368174 | A | 8/2018 |

(Continued)

OTHER PUBLICATIONS

Steinberg et al., Sequential Intravesical Gemcitabine and Docetaxel for the Salvage Treatment of Non-Muscle Invasive Bladder Cancer. Bladder Cancer. Apr. 30, 2015;1(1):65-72. (Year: 2015).*

(Continued)

*Primary Examiner* — Clinton A Brooks
*Assistant Examiner* — Izabela Schmidt
(74) *Attorney, Agent, or Firm* — BakerHostetler

(57) ABSTRACT

Described herein are methods of treating high-risk non-muscle invasive bladder cancer (HR-NMIBC) comprising administering a fibroblast growth factor receptor (FGFR) inhibitor. Also described are methods of treating intermediate risk non-muscle a invasive bladder cancer (IR-NMIBC) comprising administering an FGFR inhibitor.

45 Claims, 2 Drawing Sheets

Specification includes a Sequence Listing.

Related U.S. Application Data filed on May 1, 2020, provisional application No. 62/975,547, filed on Feb. 12, 2020.

(56) References Cited

U.S. PATENT DOCUMENTS

| | | | | |
|---|---|---|---|---|
| 4,801,531 | A | 1/1989 | Frossard | |
| 5,033,252 | A | 7/1991 | Carter | |
| 5,052,558 | A | 10/1991 | Carter | |
| 5,192,659 | A | 3/1993 | Simons | |
| 5,272,057 | A | 12/1993 | Smulson et al. | |
| 5,323,907 | A | 6/1994 | Kalvelage | |
| 5,882,864 | A | 3/1999 | An et al. | |
| 6,218,529 | B1 | 4/2001 | An et al. | |
| 11,077,106 | B2 * | 8/2021 | Stuyckens ............ | A61K 31/498 |
| 12,037,644 | B2 * | 7/2024 | Platero ................. | C12Q 1/6886 |
| 2013/0072457 | A1 | 3/2013 | Saxty et al. | |
| 2016/0287699 | A1 | 10/2016 | Karkera et al. | |
| 2017/0145102 | A1 | 5/2017 | Pierce et al. | |
| 2018/0021332 | A1 | 1/2018 | Broggini | |
| 2018/0092901 | A1 | 4/2018 | Denker et al. | |

FOREIGN PATENT DOCUMENTS

| | | | | |
|---|---|---|---|---|
| WO | 2006/000420 A1 | 1/2006 | | |
| WO | 2006/127926 A2 | 11/2006 | | |
| WO | 2008/112408 A1 | 9/2008 | | |
| WO | 2011/135376 A1 | 11/2011 | | |
| WO | 2015/144803 A1 | 10/2015 | | |
| WO | 2015/144804 A1 | 10/2015 | | |
| WO | 2015/144808 A1 | 10/2015 | | |
| WO | 2016/048833 A2 | 3/2016 | | |
| WO | 2016/128411 A1 | 8/2016 | | |
| WO | 2016/140717 A1 | 9/2016 | | |
| WO | WO-2018141921 A1 * | 8/2018 | ........... | A61K 31/498 |
| WO | 2018/220206 A1 | 12/2018 | | |
| WO | 2020/165181 A1 | 8/2020 | | |

OTHER PUBLICATIONS

Hahn NM et al., Hoosier Cancer Research Network Trial HCRN 12-157. Clin Cancer Res. Jun. 15, 2017;23(12):3003-3011 (Year: 2017).*

2019-002449-39 (A Study of Erdafitinib Versus Investigator Choice of Intravesical Chemotherapy in Participants Who Received Bacillus Calmette-Guérin (BCG) 2019. (Year: 2019).*

Kamat A. M. et al. Nat. Rev. Urol. 12, 225-235 (2015); published online Mar. 24, 2015 (Year: 2015).*

Kamat et al., (J Urol. Aug. 2014 ; 192(2): 305-315. doi:10.1016/j.juro.2014.02.2573 (Year: 2014).*

Cassell A, Yunusa B, Jalloh M, Mbodji MM, Diallo A, Ndoye M, Diallo Y, Labou I, Niang L, Gueye SM. Non-Muscle Invasive Bladder Cancer: A Review of the Current Trend in Africa. World J Oncol. Jun. 2019; 10(3):123-131. (Year: 2019).*

Angerer et al., "Demonstration of Tissue-Specific Gene Expression by in Situ Hybridization", Methods in Enzymology, 1987, vol. 152, pp. 649-661.

Anonymous, "A Study of Erdafitinib Versus Investigator Choice of Intravesical Chemotherapy in Participants Who Received Bacillus Calmette-Guerin (BCG) and Recurred with High Risk Non-Muscle-Invasive Bladder Cancer (NMIBC)", ClinicalTrials.gov Identifier: NCT04172675, first posted Nov. 21, 2019.

Ausubel et al., "Informatics for Molecular Biologists", in Current Protocols in Molecular Biology, John Wiley & Sons Inc, Chapter 19, 2004, Supplement 68, pp. 19.0.1-19.0.2.

Bartlett, "Fluorescence In Situ Hybridization: Technical Overview", Molecular Diagnosis of Cancer, Second Edition, Mar. 2004, pp. 77-87.

Bello et al., "E-3810 Is a Potent Dual Inhibitor of VEGFR and FGFR that Exerts Antitumor Activity in Multiple Preclinical Models", Cancer Res., 2011, vol. 71, No. 4, pp. 1396-1405.

Deprimo et al. "Expression Profiling of Blood Samples From an SU5416 Phase III Metastatic Colorectal Cancer Clinical Trial: A Novel Strategy for Biomarker Identification," BMC Cancer, 2003, vol. 3, No. 3, pp. 1-12.

Gavine et al., "AZD4547: An Orally Bioavailable, Potent, and Selective Inhibitor of the Fibroblast Growth Factor Receptor Tyrosine Kinase Family", Cancer Res., 2012, vol. 72, No. 8, pp. 2045-2056.

Hahn et al., "A Phase II Trial of Dovitinib in BCG-Unresponsive Urothelial Carcinoma with FGFR3 Mutations or Overexpression: Hoosier Cancer Research Network Trial HCRN 12-157", Clinical Cancer Research, 2017, vol. 23, No. 12, pp. 3003-3011.

Herr et al., "Does early cystectomy improve the survival of patients with high risk superficial bladder tumors?", J Urol, 2001, vol. 166, No. 4, pp. 1296-1299.

Innis et al., "PCR Protocols: A Guide to Methods and Applications", Academic Press, Inc., 1990, p. 1.

Isharwal et al., "Non-muscle Invasive Bladder Cancer Risk Stratification", Indian J. Urol., 2015, vol. 31, No. 4, pp. 289-296.

Knights et al., "De-Regulated FGF Receptors as Therapeutic Targets in Cancer", Pharmacology & Therapeutics, 2010, vol. 125 No. 1, pp. 105-117.

Korc et al., "The Role of Fibroblast Growth Factors in Tumor Growth", Current Cancer Drug Targets, 2009, vol. 9 No. 5, pp. 639-651.

Loriot et al., "Erdafitinib in Locally Advanced or Metastatic Urothelial Carcinoma", N. Engl. J. Med., 2019, vol. 381, pp. 338-348.

Orre et al., "VEGF, VEGFR-1, VEGFR-2, Microvessel Density and Endothelial Cell Proliferation in Tumours of the Ovary", Int. J. Cancer, 1999, vol. 84, No. 2, pp. 101-108.

Sambrook et al., "Molecular Cloning: A Laboratory Manual", 3rd Ed., Cold Spring Harbor Laboratory Press, 2001, pp. 1-21.

Siefker-Radtke et al., Efficacy of programmed death 1 (PD-1)and programmed death 1 ligand (PD-L1)inhibitors in patients with FGFR mutations and gene fusions: Results from a data analysis of an ongoing phase 2 study of erdafitinib (JNJ-42756493) in patients (pts)with advanced urothelial cancer (UC)., ASCO-GU 36, No. 6, 2018, Abstract 450, 1-4.

Siefker-Radtke, et al., ASCO, "First results from the primary analysis population of the phase 2 study of erdafitinib (ERDA; JNJ-42756493) inpatients (pts) with metastatic or unresectable urothelial carcinoma (mUC) and FGFR alterations (FGFRalt)", 36, No. 15, 2018, Abstract 4503, 1-5.

Soria et al., "Safety and Activity of the Pan-Fibroblast Growth Factor Receptor (FGFR) Inhibitor Erdafitinib in Phase 1 Study Patients With Advanced Urothelial Carcinoma", Annals of Oncology, 2016, vol. 27, Suppl. 6, pp. vi269.

Steinberg et al., "A randomized phase II study of erdafitinib (ERDA) versus intravesical chemotherapy (IC) in patients with high-risk nonmuscle invasive bladder cancer (HR-NMIBC) with FGFR mutations or fusions, who recurred after Bacillus Calmette-Guerin (BCG) therapy", Journal of Clinical Oncology, Feb. 2020, vol. 38, No. 6,.

Sylvester et al., "Predicting Recurrence and Progression in Individual Patients with Stage Ta T1 Bladder Cancer Using EORTC Risk Tables: A Combined Analysis of 2596 Patients from Seven EORTC Trials", Eur. Urol., 2006, vol. 49, pp. 466-477.

Tabernero et al., "Phase I Dose-Escalation Study of JNJ-42756493, An Oral Pan-Fibroblast Growth Factor Receptor Inhibitor, In Patients With Advanced Solid Tumors," Journal of Clinical Oncology, 2015, vol. 33, No. 30, pp. 3401-3408.

Zlotta et al., "The Management of BCG Failure In Non-Muscle-Invasive Bladder Cancer: An Update", Can Urol. Assoc. J., 2009, vol. 3, Issue 6, Supp. 4, pp. S199-S205.

A Study of Erdafitinib Versus Investigator Choice of Intravesical Chemotherapy in Participants Who Received Bacillus Calmette-Guérin (BCG) and Recurred With High Risk Non-Muscle-Invasive Bladder Cancer (NMIBC), NCT04172675, Version 4, Jan. 30, 2020, pp. 1-20.

Hepburn et al., "Side population in human non-muscle invasive bladder cancer enriches for cancer stem cells that are maintained by MAPK signalling", . PLoS ONE, vol. 7, No. 11, e50690, Nov. 2012, pp. 1-11.

(56) References Cited

OTHER PUBLICATIONS

Perera et al., "Discovery and Pharmacological Characterization of JNJ-42756493 (Erdafitinib), a Functionally Selective Small-Molecule FGFR Family Inhibitor", Mol Cancer Ther., vol. 16, No. 6, Jun. 2017, pp. 1010-1020.
"A Study to Evaluate Safety, Efficacy, Pharmacokinetics, and Pharmacodynamics of Erdafitinib Plus JNJ-63723283 (Cetrelimab), an Anti-PD-1 Monoclonal Antibody, in Participants With Metastatic or Locally Advanced Urothelial Cancer With Selected FGFR Gene Alterations", Jan. 2, 2024, pp. 1-20.
Casadei et al., "Targeted therapies for advanced bladder cancer: new strategies with FGFR inhibitors", Therapeutic Advances in Medical Oncology, Oct. 29, 2019, vol. 11, pp. 1-14.
Chang et al., Diagnosis and Treatment of Non-Muscle Invasive Bladder Cancer: AUA/SUO Guideline (2020), J. Urol. 196: 1021, 2016, https://web.archive.org/web/20221127052235/https://www.auanet.org/guidelines-and-quality/guidelines/bladder-cancer-non-muscle-invasive-guideline, downloaded Apr. 10, 2026, 33 pages.

* cited by examiner

SEQUENCE LISTING

```
<160> NUMBER OF SEQ ID NOS: 38

<210> SEQ ID NO 1
<211> LENGTH: 268
<212> TYPE: DNA
<213> ORGANISM: Homo sapiens
```

<400> SEQUENCE: 1
tcggaccgcg gcaactacac ctgcgtcgtg gagaacaagt ttggcagcat ccggcagacg 60
tacacgctgg acgtgctgga gtgctccccg caccggccca tcctgcaggc ggggctgccg 120
gccaaccaga cggcggtgct gggcagcgac gtggagttcc actgcaaggt gtacagtgac 180
gcacagcccc acatccagtg gctcaagcac gtggaggtga atggcagcaa ggtgggcccg 240
gacggcacac cctacgttac cgtgctca 268

<210> SEQ ID NO 2
<211> LENGTH: 378
<212> TYPE: DNA
<213> ORGANISM: Homo sapiens

<400> SEQUENCE: 2
gaccgcggca actacacctg cgtcgtggag aacaagtttg gcagcatccg gcagacgtac 60
acgctggacg tgctgggtga gggccctggg gcggcgcggg ggtgggggcg gcagtggcgg 120
tggtggtgag ggagggggtg gcccctgagc gtcatctgcc cccacagagc gctgcccgca 180
ccggcccatc ctgcaggcgg ggctgccggc caaccagacg gcggtgctgg gcagcgacgt 240
ggagttccac tgcaaggtgt acagtgacgc acagccccac atccagtggc tcaagcacgt 300
ggaggtgaat ggcagcaagg tgggcccgga cggcacaccc tacgttaccg tgctcaaggt 360
gggccaccgt gtgcacgt 378

<210> SEQ ID NO 3
<211> LENGTH: 234
<212> TYPE: DNA
<213> ORGANISM: Homo sapiens

<400> SEQUENCE: 3
gcgggcaatt ctattgggtt ttctcatcac tctgcgtggc tggtggtgct gccagccgag 60
gaggagctgg tggaggctga cgaggcgtgc agtgtgtatg caggcatcct cagctacggg 120
gtgggcttct tcctgttcat cctggtggtg gcggctgtga cgctctgccg cctgcgcagc 180
ccccccaaga aaggcctggg ctcccccacc gtgcacaaga tctcccgctt cccg 234

<210> SEQ ID NO 4
<211> LENGTH: 301
<212> TYPE: DNA
<213> ORGANISM: Homo sapiens

<400> SEQUENCE: 4
ctagaggttc tctccttgca caacgtcacc tttgaggacg ccggggagta cacctgcctg 60
gcgggcaatt ctattgggtt ttctcatcac tctgcgtggc tggtggtgct gccagccgag 120
gaggagctgg tggaggctga cgaggcgggc agtgtgtgtg caggcatcct cagctacggg 180
gtgggcttct tcctgttcat cctggtggtg gcggctgtga cgctctgccg cctgcgcagc 240
ccccccaaga aaggcctggg ctcccccacc gtgcacaaga tctcccgctt cccgctcaag 300
c 301

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gacctggacc gtgtccttac c 21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
cttccccagt tccaggttct t 21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
aggacctgga ccgtgtcctt 20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
tataggtccg gtggacaggg 20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ctggaccgtg tccttaccgt 20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcagcccagg attgaactgt 20

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
tggatcgaat tctcactctc aca 23

<210> SEQ ID NO 12
<211> LENGTH: 21

<212> TYPE: DNA
<213> ORGANISM: Artificial Sequence
<220> FEATURE:
<223> OTHER INFORMATION: Synthetic primer

<400> SEQUENCE: 12
gccaagcaat ctgcgtattt g 21

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gctcttcaat acagccctga tca 23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
acttggatcg aattctcact ctca 24

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
tggatcgaat tctcactctc aca 23

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
gcaaagcctg aattttcttg aataa 25

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
gcatccggca gacgtaca 18

<210> SEQ ID NO 18
<211> LENGTH: 15
<212> TYPE: DNA
<213> ORGANISM: Artificial Sequence
<220> FEATURE:
<223> OTHER INFORMATION: Synthetic primer

<400> SEQUENCE: 18
ccccgcctgc aggat 15

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gcatccggca gacgtaca 18

<210> SEQ ID NO 20
<211> LENGTH: 15
<212> TYPE: DNA
<213> ORGANISM: Artificial Sequence
<220> FEATURE:
<223> OTHER INFORMATION: Synthetic primer

<400> SEQUENCE: 20
ccccgcctgc aggat 15

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
aggagctggt ggaggctga 19

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
ccgtagctga ggatgcctg 19

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
ctggtggagg ctgacgag 18

<210> SEQ ID NO 24
<211> LENGTH: 16
<212> TYPE: DNA
<213> ORGANISM: Artificial Sequence
<220> FEATURE:
<223> OTHER INFORMATION: Synthetic primer

<400> SEQUENCE: 24
agcccacccc gtagct 16

<210> SEQ ID NO 25

-continued

<211> LENGTH: 21
<212> TYPE: DNA
<213> ORGANISM: Artificial Sequence
<220> FEATURE:
<223> OTHER INFORMATION: Synthetic primer

<400> SEQUENCE: 25
gtcgtggaga acaagtttgg c 21

<210> SEQ ID NO 26
<211> LENGTH: 17
<212> TYPE: DNA
<213> ORGANISM: Artificial Sequence
<220> FEATURE:
<223> OTHER INFORMATION: Synthetic primer

<400> SEQUENCE: 26
gtctggttgg ccggcag 17

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
gtcgtggaga acaagtttgg c 21

<210> SEQ ID NO 28
<211> LENGTH: 17
<212> TYPE: DNA
<213> ORGANISM: Artificial Sequence
<220> FEATURE:
<223> OTHER INFORMATION: Synthetic primer

<400> SEQUENCE: 28
gtctggttgg ccggcag 17

<210> SEQ ID NO 29
<211> LENGTH: 19
<212> TYPE: DNA
<213> ORGANISM: Artificial Sequence
<220> FEATURE:
<223> OTHER INFORMATION: synthetic primer

<400> SEQUENCE: 29
aggagctggt ggaggctga 19

<210> SEQ ID NO 30
<211> LENGTH: 19
<212> TYPE: DNA
<213> ORGANISM: Artificial Sequence
<220> FEATURE:
<223> OTHER INFORMATION: Synthetic primer

<400> SEQUENCE: 30
ccgtagctga ggatgcctg 19

<210> SEQ ID NO 31
<211> LENGTH: 16
<212> TYPE: DNA
<213> ORGANISM: Artificial Sequence
<220> FEATURE:
<223> OTHER INFORMATION: Synthetic primer -continued

<400> SEQUENCE: 31
gacgaggcgg gcagtg 16

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
gaagaagccc accccgtag 19

<210> SEQ ID NO 33
<211> LENGTH: 2850
<212> TYPE: DNA
<213> ORGANISM: Artificial Sequence
<220> FEATURE:
<223> OTHER INFORMATION: Synthetic polynucleotide

<400> SEQUENCE: 33
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380 gccgaccccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560

```
gacctggtgt ctgagatgga gatgatgaag atgatcggga aacacaaaaa catcatcaac   1620

ctgctgggcg cctgcacgca gggcgggccc ctgtacgtgc tggtggagta cgcggccaag   1680

ggtaacctgc gggagtttct gcgggcgcgg cggcccccgg gcctggacta ctccttcgac   1740

acctgcaagc cgcccgagga gcagctcacc ttcaaggacc tggtgtcctg tgcctaccag   1800

gtggcccggg gcatggagta cttggcctcc cagaagtgca tccacaggga cctggctgcc   1860

cgcaatgtgc tggtgaccga ggacaacgtg atgaagatcg cagacttcgg gctggcccgg   1920

gacgtgcaca acctcgacta ctacaagaag acgaccaacg gccggctgcc cgtgaagtgg   1980

atggcgcctg aggccttgtt tgaccgagtc tacactcacc agagtgacgt ctggtccttt   2040

ggggtcctgc tctgggagat cttcacgctg gggggctccc cgtaccccgg catccctgtg   2100

gaggagctct tcaagctgct gaaggagggc caccgcatgg acaagcccgc caactgcaca   2160

cacgacctgt acatgatcat gcgggagtgc tggcatgccg cgccctccca gaggcccacc   2220

ttcaagcagc tggtggagga cctggaccgt gtccttaccg tgacgtccac cgacgtaaag   2280

gcgacacagg aggagaaccg ggagctgagg agcaggtgtg aggagctcca cgggaagaac   2340

ctggaactgg ggaagatcat ggacaggttc gaagaggttg tgtaccaggc catggaggaa   2400

gttcagaagc agaaggaact ttccaaagct gaaatccaga aagttctaaa agaaaaagac   2460

caacttacca cagatctgaa ctccatggag aagtccttct ccgacctctt caagcgtttt   2520

gagaaacaga aagaggtgat cgagggctac cgcaagaacg aagagtcact gaagaagtgc   2580

gtggaggatt acctggcaag gatcacccag gagggccaga ggtaccaagc cctgaaggcc   2640

cacgcggagg agaagctgca gctggcaaac gaggagatcg cccaggtccg gagcaaggcc   2700

caggcggaag cgttggccct ccaggccagc ctgaggaagg agcagatgcg catccagtcg   2760

ctggagaaga cagtggagca gaagactaaa gagaacgagg agctgaccag gatctgcgac   2820

gacctcatct ccaagatgga gaagatctga                                   2850
```

<210> SEQ ID NO 34
<211> LENGTH: 2955
<212> TYPE: DNA
<213> ORGANISM: Artificial Sequence
<220> FEATURE:
<223> OTHER INFORMATION: Synthetic polynucleotide

<400> SEQUENCE: 34

```
atgggcgccc ctgcctgcgc cctcgcgctc tgcgtggccg tggccatcgt ggccggcgcc     60

tcctcggagt ccttggggac ggagcagcgc gtcgtggggc gagcggcaga agtcccgggc    120

ccagagcccg gccagcagga gcagttggtc ttcggcagcg gggatgctgt ggagctgagc    180

tgtcccccgc ccgggggtgg tcccatgggg cccactgtct gggtcaagga tggcacaggg    240

ctggtgccct cggagcgtgt cctggtgggg ccccagcggc tgcaggtgct gaatgcctcc    300

cacgaggact ccggggccta cagctgccgg cagcggctca cgcagcgcgt actgtgccac    360

ttcagtgtgc gggtgacaga cgctccatcc tcgggagatg acgaagacgg ggaggacgag    420

gctgaggaca caggtgtgga cacaggggcc ccttactgga cacggcccga gcggatggac    480

aagaagctgc tggccgtgcc ggccgccaac accgtccgct tccgctgccc agccgctggc    540

aaccccactc cctccatctc ctggctgaag aacggcaggg agttccgcgg cgagcaccgc    600

attggaggca tcaagctgcg gcatcagcag tggagcctgg tcatggaaag cgtggtgccc    660

tcggaccgcg gcaactacac ctgcgtcgtg gagaacaagt ttggcagcat ccggcagacg    720

tacacgctgg acgtgctgga gcgctccccg caccggccca tcctgcaggc ggggctgccg    780
```

gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acgaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg gggggctccc cgtaccccgg catccctgtg 2100
gaggagctct tcaagctgct gaaggagggc caccgcatgg acaagcccgc caactgcaca 2160
cacgacctgt acatgatcat gcgggagtgc tggcatgccg cgccctccca gaggcccacc 2220
ttcaagcagc tggtggagga cctggaccgt gtccttaccg tgacgtccac cgacgtgcca 2280
ggcccacccc caggtgttcc cgcgcctggg ggcccacccc tgtccaccgg acctatagtg 2340
gacctgctcc agtacagcca gaaggacctg gatgcagtgg taaaggcgac acaggaggag 2400
aaccgggagc tgaggagcag gtgtgaggag ctccacggga agaacctgga actggggaag 2460
atcatggaca ggttcgaaga ggttgtgtac caggccatgg aggaagttca gaagcagaag 2520
gaactttcca aagctgaaat ccagaaagtt ctaaaagaaa aagaccaact taccacagat 2580
ctgaactcca tggagaagtc cttctccgac ctcttcaagc gttttgagaa acagaaagag 2640
gtgatcgagg gctaccgcaa gaacgaagag tcactgaaga agtgcgtgga ggattacctg 2700
gcaaggatca cccaggaggg ccagaggtac caagccctga aggcccacgc ggaggagaag 2760
ctgcagctgg caaacgagga gatcgcccag gtccggagca aggcccaggc ggaagcgttg 2820
gccctccagg ccagcctgag gaaggagcag atgcgcatcc agtcgctgga gaagacagtg 2880
gagcagaaga ctaaagagaa cgaggagctg accaggatct gcgacgacct catctccaag 2940
atggagaaga tctga 2955

<210> SEQ ID NO 35
<211> LENGTH: 3765
<212> TYPE: DNA

<213> ORGANISM: Artificial Sequence
<220> FEATURE:
<223> OTHER INFORMATION: Synthetic polynucleotide

<400> SEQUENCE: 35
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag tcctggatca gtgagagtgt ggaggccgac 960
gtgcgcctcc gcctggccaa tgtgtcggag cgggacgggg gcgagtacct ctgtcgagcc 1020
accaatttca taggcgtggc cgagaaggcc ttttggctga gcgttcacgg gccccgagca 1080
gccgaggagg agctggtgga ggctgacgag gcgggcagtg tgtatgcagg catcctcagc 1140
tacggggtgg gcttcttcct gttcatcctg gtggtggcgg ctgtgacgct ctgccgcctg 1200
cgcagccccc ccaagaaagg cctgggctcc ccccaccgtgc acaagatctc ccgcttcccg 1260
ctcaagcgac aggtgtccct ggagtccaac gcgtccatga gctccaacac accactggtg 1320
cgcatcgcaa ggctgtcctc aggggagggc cccacgctgg ccaatgtctc cgagctcgag 1380
ctgcctgccg accccaaatg ggagctgtct cgggcccggc tgaccctggg caagcccctt 1440
ggggagggct gcttcggcca ggtggtcatg gcggaggcca tcggcattga caaggaccgg 1500
gccgccaagc ctgtcaccgt agccgtgaag atgctgaaag acgatgccac tgacaaggac 1560
ctgtcggacc tggtgtctga gatggagatg atgaagatga tcgggaaaca caaaaacatc 1620
atcaacctgc tgggcgcctg cacgcagggc gggcccctgt acgtgctggt ggagtacgcg 1680
gccaagggta acctgcggga gtttctgcgg gcgcggcggc ccccgggcct ggactactcc 1740
ttcgacacct gcaagccgcc cgaggagcag ctcaccttca aggacctggt gtcctgtgcc 1800
taccaggtgg cccggggcat ggagtacttg gcctcccaga agtgcatcca cagggacctg 1860
gctgcccgca atgtgctggt gaccgaggac aacgtgatga agatcgcaga cttcgggctg 1920
gcccgggacg tgcacaacct cgactactac aagaagacga ccaacggccg gctgcccgtg 1980
aagtggatgg cgcctgaggc cttgtttgac cgagtctaca ctcaccagag tgacgtctgg 2040
tcctttgggg tcctgctctg ggagatcttc acgctggggg gctccccgta ccccggcatc 2100
cctgtggagg agctcttcaa gctgctgaag gagggccacc gcatggacaa gcccgccaac 2160
tgcacacacg acctgtacat gatcatgcgg gagtgctggc atgccgcgcc ctcccagagg 2220

-continued cccaccttca agcagctggt ggaggacctg gaccgtgtcc ttaccgtgac gtccaccgac 2280
aatgttatgg aacagttcaa tcctgggctg cgaaatttaa taaacctggg gaaaaattat 2340
gagaaagctg taaacgctat gatcctggca ggaaaagcct actacgatgg agtggccaag 2400
atcggtgaga ttgccactgg gtcccccgtg tcaactgaac tgggacatgt cctcatagag 2460
atttcaagta cccacaagaa actcaacgag agtcttgatg aaaattttaa aaaattccac 2520
aaagagatta tccatgagct ggagaagaag atagaacttg acgtgaaata tatgaacgca 2580
actctaaaaa gataccaaac agaacacaag aataaattag agtctttgga gaaatcccaa 2640
gctgagttga agaagatcag aaggaaaagc caaggaagcc gaaacgcact caaatatgaa 2700
cacaaagaaa ttgagtatgt ggagaccgtt acttctcgtc agagtgaaat ccagaaattc 2760
attgcagatg gttgcaaaga ggctctgctt gaagagaaga ggcgcttctg ctttctggtt 2820
gataagcact gtggctttgc aaaccacata cattattatc acttacagtc tgcagaacta 2880
ctgaattcca agctgcctcg gtggcaggag acctgtgttg atgccatcaa agtgccagag 2940
aaaatcatga atatgatcga agaaataaag accccagcct ctaccccccgt gtctggaact 3000 cctcaggctt cacccatgat cgagagaagc aatgtggtta ggaaagatta cgacaccctt 3060
tctaaatgct caccaaagat gcccccccgct ccttcaggca gagcatatac cagtcccttg 3120
atcgatatgt ttaataaccc agccacggct gccccgaatt cacaaagggt aaataattca 3180
acaggtactt ccgaagatcc cagtttacag cgatcagttt cggttgcaac gggactgaac 3240
atgatgaaga agcagaaagt gaagaccatc ttcccgcaca ctgcgggctc caacaagacc 3300
ttactcagct ttgcacaggg agatgtcatc acgctgctca tccccgagga gaaggatggc 3360
tggctctatg gagaacacga cgtgtccaag gcgaggggtt ggttcccgtc gtcgtacacg 3420
aagttgctgg aagaaaatga gacagaagca gtgaccgtgc ccacgccaag ccccacacca 3480
gtgagaagca tcagcaccgt gaacttgtct gagaatagca gtgttgtcat ccccccaccc 3540
gactacttgg aatgcttgtc catgggggca gctgccgaca ggagagcaga ttcggccagg 3600
acgacatcca cctttaaggc cccagcgtcc aagcccgaga ccgcggctcc taacgatgcc 3660
aacgggactg caaagccgcc ttttctcagc ggagaaaacc cctttgccac tgtgaaactc 3720
cgcccgactg tgacgaatga tcgctcggca cccatcattc gatga 3765

<210> SEQ ID NO 36
<211> LENGTH: 4989
<212> TYPE: DNA
<213> ORGANISM: Artificial Sequence
<220> FEATURE:
<223> OTHER INFORMATION: Synthetic polynucleotide

<400> SEQUENCE: 36
atggtcagct ggggtcgttt catctgcctg gtcgtggtca ccatggcaac cttgtccctg 60
gcccggccct ccttcagttt agttgaggat accacattag agccagaaga gccaccaacc 120
aaataccaaa tctctcaacc agaagtgtac gtggctgcgc caggggagtc gctagaggtg 180
cgctgcctgt tgaaagatgc cgccgtgatc agttggacta aggatggggt gcacttgggg 240
cccaacaata ggacagtgct tattggggag tacttgcaga taaagggcgc cacgcctaga 300
gactccggcc tctatgcttg tactgccagt aggactgtag acagtgaaac ttggtacttc 360
atggtgaatg tcacagatgc catctcatcc ggagatgatg aggatgacac cgatggtgcg 420
gaagattttg tcagtgagaa cagtaacaac aagagagcac catactggac caacacagaa 480

-continued

```
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatcatggag gaaacaaata cgcagattgc ttggccatca   2340
aaactgaaga tcggagccaa atccaagaaa gatccccata ttaaggtttc tggaaagaaa   2400
gaagatgtta aagaagccaa ggaaatgatc atgtctgtct tagacacaaa aagcaatcga   2460
gtcacactga agatggatgt ttcacataca gaacattcac atgtaatcgg caaaggtggc   2520
aacaatatta aaaaagtgat ggaagaaacc ggatgccata tccactttcc agattccaac   2580
aggaataacc aagcagaaaa aagcaaccag gtatctatag cgggacaacc agcaggagta   2640
gaatctgccc gagttagaat tcgggagctg cttcctttgg tgctgatgtt tgagctacca   2700
attgctggaa ttcttcaacc ggttcctgat cctaattccc cctctattca gcatatatca   2760
caaacgtaca atatttcagt atcatttaaa cagcgttccc gaatgtatgg tgctactgtc   2820
atagtacgag ggtctcagaa taacactagt gctgtgaagg aaggaactgc catgctgtta   2880
```

gaacatcttg ctgggagctt agcatcagct attcctgtga gcacacaact agatattgca 2940
gctcaacatc atctctttat gatgggtcga aatgggagca acatcaaaca tatcatgcag 3000
agaacaggtg ctcagatcca ctttcctgat cccagtaatc cacaaaagaa atctaccgtc 3060
tacctccagg gcaccattga gtctgtctgt cttgcaaggc aatatctcat gggttgtctt 3120
cctcttgtgt tgatgtttga tatgaaggaa gaaattgaag tagatccaca attcattgcg 3180
cagttgatgg aacagcttga tgtcttcatc agtattaaac caaagcccaa acagccaagc 3240
aagtctgtga ttgtgaaaag tgttgagcga aatgccttaa atatgtatga agcaaggaaa 3300
tgtctcctcg gacttgaaag cagtggggtt accatagcaa ccagtccatc cccagcatcc 3360
tgccctgccg gcctggcatg tcccagcctg gatatcttag cttcagcagg ccttggactc 3420
actggactag gtcttttggg acccaccacc ttatctctga acacttcaac aaccccaaac 3480
tcactcttga atgctcttaa tagctcagtc agtcctttgc aaagtccaag ttctggtaca 3540
cccagcccca cattatgggc acccccactt gctaatactt caagtgccac aggtttttct 3600
gctataccac accttatgat tccatctact gcccaagcca cattaactaa tattttgttg 3660
tctggagtgc ccacctatgg gcacacagct ccatctcccc ctcctggctt gactcctgtt 3720
gatgtccata tcaacagtat gcagaccgaa ggcaaaaaaa tctctgctgc tttaaatgga 3780
catgcacagt ctccagatat aaaatatggt gcaatatcca cttcatcact tggagaaaaa 3840
gtgctgagtg caaatcacgg ggatccgtcc atccagacaa gtgggtctga gcagacatct 3900
cccaaatcaa gccccactga aggttgtaat gatgcttttg ttgaagtagg catgcctcga 3960
agtccttccc attctgggaa tgctggtgac ttgaaacaga tgatgtgtcc ctccaaggtt 4020
tcctgtgcca aaaggcagac agtggaacta ttgcaaggca cgaaaaactc acacttacac 4080
agcactgaca ggttgctctc agaccctgaa ctgagtgcta ccgaaagccc tttggctgac 4140
aagaaggctc cagggagtga gcgcgctgca gagagggcag cagctgccca gcaaaactcc 4200
gaaagggccc accttgctcc acggtcatca tatgtcaaca tgcaggcatt tgactatgaa 4260
cagaagaagc tattagccac caaagctatg ttaaagaaac cagtggtgac ggaggtcaga 4320
acgcccacaa atacctggag tggcctgggt ttttctaaat ccatgccagc tgaaactatc 4380
aaggagttga gaagggccaa tcatgtgtcc tataagccca caatgacaac cacttatgag 4440
ggctcatcca tgtccctttc acggtccaac agtcgtgagc acttgggagg tggaagcgaa 4500
tctgataact ggagagaccg aaatggaatt ggacctggaa gtcatagtga atttgcagct 4560
tctattggca gccctaagcg taaacaaaac aaatcaacgg aacactatct cagcagtagc 4620
aattacatgg actgcatttc ctcgctgaca ggaagcaatg gctgtaactt aaatagctct 4680
ttcaaaggtt ctgacctccc tgagctcttc agcaaactgg gcctgggcaa atacacagat 4740
gttttccagc aacaagagat cgatcttcag acattcctca ctctcacaga tcaggatctg 4800
aaggagctgg gaataactac ttttggtgcc aggaggaaaa tgctgcttgc aatttcagaa 4860
ctaaataaaa accgaagaaa gctttttgaa tcgccaaatg cacgcacctc tttcctggaa 4920
ggtggagcga gtggaaggct accccgtcag tatcactcag acattgctag tgtcagtggc 4980
cgctggtag 4989

<210> SEQ ID NO 37
<211> LENGTH: 3213
<212> TYPE: DNA
<213> ORGANISM: Artificial Sequence
<220> FEATURE:

-continued

<223> OTHER INFORMATION: Synthetic polynucleotide

<400> SEQUENCE: 37
atggtcagct ggggtcgttt catctgcctg gtcgtggtca ccatggcaac cttgtccctg 60
gcccggccct ccttcagttt agttgaggat accacattag agccagaaga gccaccaacc 120
aaataccaaa tctctcaacc agaagtgtac gtggctgcgc caggggagtc gctagaggtg 180
cgctgcctgt tgaaagatgc cgccgtgatc agttggacta aggatggggt gcacttgggg 240
cccaacaata ggacagtgct tattggggag tacttgcaga taaagggcgc cacgcctaga 300
gactccggcc tctatgcttg tactgccagt aggactgtag acagtgaaac ttggtacttc 360
atggtgaatg tcacagatgc catctcatcc ggagatgatg aggatgacac cgatggtgcg 420
gaagattttg tcagtgagaa cagtaacaac aagagagcac catactggac caacacagaa 480
aagatggaaa agcggctcca tgctgtgcct gcggccaaca ctgtcaagtt tcgctgccca 540
gccgggggga acccaatgcc aaccatgcgg tggctgaaaa acgggaagga gtttaagcag 600
gagcatcgca ttggaggcta caaggtacga aaccagcact ggagcctcat tatggaaagt 660
gtggtcccat ctgacaaggg aaattatacc tgtgtagtgg agaatgaata cgggtccatc 720
aatcacacgt accacctgga tgttgtggag cgatcgcctc accggcccat cctccaagcc 780
ggactgccgg caaatgcctc cacagtggtc ggaggagacg tagagtttgt ctgcaaggtt 840
tacagtgatg cccagcccca catccagtgg atcaagcacg tggaaaagaa cggcagtaaa 900
tacgggcccg acgggctgcc ctacctcaag gttctcaagg ccgccggtgt taacaccacg 960
gacaaagaga ttgaggttct ctatattcgg aatgtaactt ttgaggacgc tggggaatat 1020
acgtgcttgg cgggtaattc tattgggata tcctttcact ctgcatggtt gacagttctg 1080
ccagcgcctg gaagagaaaa ggagattaca gcttccccag actacctgga gatagccatt 1140
tactgcatag gggtcttctt aatcgcctgt atggtggtaa cagtcatcct gtgccgaatg 1200
aagaacacga ccaagaagcc agacttcagc agccagccgg ctgtgcacaa gctgaccaaa 1260
cgtatccccc tgcggagaca ggtaacagtt tcggctgagt ccagctcctc catgaactcc 1320
aacaccccgc tggtgaggat aacaacacgc ctctcttcaa cggcagacac ccccatgctg 1380
gcaggggtct ccgagtatga acttccagag gacccaaaat gggagtttcc aagagataag 1440
ctgacactgg gcaagcccct gggagaaggt tgctttgggc aagtggtcat ggcggaagca 1500
gtgggaattg acaaagacaa gcccaaggag gcggtcaccg tggccgtgaa gatgttgaaa 1560
gatgatgcca cagagaaaga cctttctgat ctggtgtcag agatggagat gatgaagatg 1620
attgggaaac acaagaatat cataaatctt cttggagcct gcacacagga tgggcctctc 1680
tatgtcatag ttgagtatgc ctctaaaggc aacctccgag aatacctccg agcccggagg 1740
ccacccggga tggagtactc ctatgacatt aaccgtgttc ctgaggagca gatgaccttc 1800
aaggacttgg tgtcatgcac ctaccagctg gccagaggca tggagtactt ggcttcccaa 1860
aaatgtattc atcgagattt agcagccaga aatgttttgg taacagaaaa caatgtgatg 1920
aaaatagcag actttggact cgccagagat atcaacaata tagactatta caaaaagacc 1980
accaatgggc ggcttccagt caagtggatg gctccagaag ccctgtttga tagagtatac 2040
actcatcaga gtgatgtctg gtccttcggg gtgttaatgt gggagatctt cactttaggg 2100
ggctcgccct acccagggat tcccgtggag gaacttttta agctgctgaa ggaaggacac 2160
agaatggata agccagccaa ctgcaccaac gaactgtaca tgatgatgag ggactgttgg 2220
catgcagtgc cctcccagag accaacgttc aagcagttgg tagaagactt ggatcgaatt 2280

-continued

```
ctcactctca caaccaatga gatggcagat gatcagggct gtattgaaga gcagggggtt   2340

gaggattcag caaatgaaga ttcagtggat gctaagccag accggtcctc gtttgtaccg   2400

tccctcttca gtaagaagaa gaaaaatgtc accatgcgat ccatcaagac cacccgggac   2460

cgagtgccta catatcagta caacatgaat tttgaaaagc tgggcaaatg catcataata   2520

aacaacaaga actttgataa agtgacaggt atgggcgttc gaaacggaac agacaaagat   2580

gccgaggcgc tcttcaagtg cttccgaagc ctgggttttg acgtgattgt ctataatgac   2640

tgctcttgtg ccaagatgca agatctgctt aaaaaagctt ctgaagagga ccatacaaat   2700

gccgcctgct tcgcctgcat cctcttaagc catggagaag aaaatgtaat ttatgggaaa   2760

gatggtgtca caccaataaa ggatttgaca gcccacttta gggggggatag atgcaaaacc   2820

cttttagaga aacccaaact cttcttcatt caggcttgcc gagggaccga gcttgatgat   2880

ggcatccagg ccgactcggg gcccatcaat gacacagatg ctaatcctcg atacaagatc   2940

ccagtggaag ctgacttcct cttcgcctat tccacggttc caggctatta ctcgtggagg   3000

agcccaggaa gaggctcctg gtttgtgcaa gccctctgct ccatcctgga ggagcacgga   3060

aaagacctgg aaatcatgca gatcctcacc agggtgaatg acagagttgc caggcacttt   3120

gagtctcagt ctgatgaccc acacttccat gagaagaagc agatcccctg tgtggtctcc   3180

atgctcacca aggaactcta cttcagtcaa tag                                3213


<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38

tttttttttt tttttttttt tttt                                           24
```

FGFR TYROSINE KINASE INHIBITORS FOR THE TREATMENT OF HIGH-RISK NON-MUSCLE INVASIVE BLADDER CANCER

CROSS-REFERENCE TO RELATED APPLICATIONS

This application is the National Stage of International Patent Application No. PCT/EP2021/053385, filed Feb. 11, 2021, which claims the benefit of U.S. Provisional Ser. No. 62/975,547, filed Feb. 12, 2020, U.S. Provisional Ser. No. 63/018,914, filed May 1, 2020, U.S. Provisional Ser. No. 63/118,475, filed Nov. 25, 2020, the disclosures of which are incorporated herein by reference in their entireties.

SEQUENCE LISTING

The instant application contains a Sequence Listing which is being submitted herewith electronically in ASCII format and is hereby incorporated by reference in its entirety. Said ASCII copy, created on Aug. 12, 2022, is named 103693_003702_SL.txt and is 31,474 bytes in size.

TECHNICAL FIELD

Disclosed herein are methods of treating high-risk non-muscle invasive bladder cancer (HR-NMIBC) comprising administering a fibroblast growth factor receptor (FGFR) inhibitor. Also disclosed are methods of treating intermediate risk non-muscle invasive bladder cancer (IR-NMIBC) comprising administering an FGFR inhibitor.

BACKGROUND

Early stage non-muscle invasive bladder cancer (NMIBC) is diagnosed in 70% of bladder cancer patients (Isharwal S, Konety B. *Indian J Urol.* 2015; 31(4):289-296) of which 25% patients have poorly differentiated, low-stage tumors known as high risk non-muscle invasive bladder cancer (HR-NMIBC). Herr H W, Sogani P C. *J Urol.* 2001; 166 (4):1296-1299. HR-NMIBC is associated with high rates of recurrence, progression to muscle invasion, and metastasis. Sylvester R J et al. *Eur Urol.* 2006; 49:466-477. The failure rate of treatment with intravesical Bacillus Calmette-Guerin (BCG) therapy is high and recurrence is observed in about 30-40% of patients. Zlotta A R et al. *Can Urol Assoc J.* 2009: S199-S205. Erdafitinib, an oral pan-FGFR kinase inhibitor, is approved by the U.S. FDA for the treatment of adult patients with locally advanced or metastatic urothelial carcinoma (mUC) which has susceptible FGFR3 or FGFR2 genetic alterations and who have progressed during or following at least one line of prior platinum-containing chemotherapy (PCC), including within 12 months of neo-adjuvant or adjuvant PCC. Loriot Y et al. *N Engl J Med.* 2019; 381:338-348.

New cancer treatment methods are needed for FGFR mutation or fusion positive HR-NMIBC or IR-NMIBC patients, who recurred after BCG therapy.

SUMMARY

Described herein are methods of treating HR-NMIBC comprising, consisting of, or consisting essentially of, for example, administering an FGFR inhibitor, in particular at a dose of about 8 mg per day, in particular erdafitinib, more in particular erdafitinib at a dose of about 8 mg per day, to a patient that has been diagnosed with HR-NMIBC who harbors at least one FGFR2 genetic alteration and/or FGFR3 genetic alteration. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein are methods of treating IR-NMIBC comprising, consisting of, or consisting essentially of, for example, administering an FGFR inhibitor, in particular at a dose of about 8 mg per day, in particular erdafitinib, more in particular erdafitinib at a dose of about 8 mg per day, to a patient that has been diagnosed with IR-NMIBC who harbors at least one FGFR2 genetic alteration and/or FGFR3 genetic alteration. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with HR-NMIBC who harbors at least one FGFR2 genetic alteration and/or FGFR3 genetic alteration. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with IR-NMIBC who harbors at least one FGFR2 genetic alteration and/or FGFR3 genetic alteration. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day. In certain embodiments, the patient received BCG therapy prior to said administration of said FGFR inhibitor. In further embodiments, the BCG therapy is adequate BCG therapy. In some embodiments, the patient is unresponsive to BCG therapy. In still further embodiments, the patient is BCG experienced. In certain embodiments, the patient has a papillary tumor. In further embodiments, the patient has carcinoma in situ. In some embodiments, the patient did not previously receive or is ineligible for a cystectomy. In an embodiment, the FGFR inhibitor is administered or is to be administered at a dose of about 6 mg per day, in particular erdafitinib, more in particular erdafitinib at a dose of about 6 mg per day.

In further embodiments, said administration of the FGFR inhibitor provides an increase in recurrence-free survival relative to a patient population with HR-NMIBC that has been administered a placebo. In certain embodiments, said administration of the FGFR inhibitor provides an increase in recurrence-free survival relative to a patient population with HR-NMIBC that has been administered intravesical gemcitabine or intravesical Mitomycin C (MMC)/hyperthermic MMC. In some embodiments, the patient exhibits a complete response to the FGFR inhibitor at about 6 months. In some embodiments, said administration of the FGFR inhibitor provides prevention or delay of disease recurrence in the non-muscle invasive bladder cancer (NMIBC) population (HR-NMIBC or IR-NMIBC).

In certain embodiments, the FGFR2 genetic alteration and/or FGFR3 genetic alteration is an FGFR3 gene mutation, FGFR2 gene fusion, or FGFR3 gene fusion. In some embodiments, the FGFR3 gene mutation is R248C, S249C, G370C, Y373C, or any combination thereof. In still further embodiments, the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.

In some embodiments, said methods or uses further comprise evaluating a biological sample from the patient for the presence of at least one of a FGFR2 genetic alteration and/or FGFR3 genetic alteration prior to said administration of the FGFR inhibitor. In certain embodiments, the biological sample is blood, lymph fluid, bone marrow, a solid tumor sample, urine or any combination thereof. In certain embodiments, the biological sample is a blood sample. In certain embodiments, the biological sample is a urine sample.

In some embodiments, the FGFR inhibitor is erdafitinib. In further embodiments, erdafitinib is administered daily, in particular once daily. In still further embodiments, erdafitinib is administered orally. In certain embodiments, erdafitinib is administered orally on a continuous daily dosing schedule. In some embodiments, erdafitinib is administered orally at a dose of about 8 mg once daily. In some embodiments, erdafitinib is administered orally at a dose of about 8 mg once daily on a continuous daily dosing schedule. In further embodiments, the dose of erdafitinib is increased from 8 mg per day to 9 mg per day after initiating treatment if the patient exhibits a serum phosphate ($PO_4$) level that is less than about 5.5 mg/dL, in particular the dose of erdafitinib is increased from 8 mg per day to 9 mg per day after initiating treatment if the patient exhibits a serum phosphate ($PO_4$) level that is less than about 5.5 mg/dL at 14-21 days after initiating treatment. In certain embodiments, erdafitinib is present in a solid dosage form. In further embodiments, the solid dosage form is a tablet.

In some embodiments, in the methods and uses as described herein, the FGFR inhibitor, in particular erdafitinib, is administered at a dose of about 6 mg per day. In further embodiments, erdafitinib is administered at a dose of about 6 mg once daily. In still further embodiments, erdafitinib is administered orally. In certain embodiments, erdafitinib is administered orally on a continuous daily dosing schedule. In some embodiments, erdafitinib is administered orally at a dose of about 6 mg once daily. In some embodiments, erdafitinib is administered orally at a dose of about 6 mg once daily on a continuous daily dosing schedule. In further embodiments, the dose of erdafitinib is increased from 6 mg per day to 8 mg per day after initiating treatment if the patient exhibits a serum phosphate ($PO_4$) level that is less than about 5.5 mg/dL, in particular the dose of erdafitinib is increased from 6 mg per day to 8 mg per day after initiating treatment if the patient exhibits a serum phosphate ($PO_4$) level that is less than about 5.5 mg/dL at 14-21 days after initiating treatment. In certain embodiments, erdafitinib is present in a solid dosage form. In further embodiments, the solid dosage form is a tablet.

Also described herein are methods of treating HR-NMIBC comprising (a) evaluating a biological sample from a patient that has been diagnosed with HR-NMIBC for the presence of one or more FGFR gene alterations, in particular one or more FGFR2 or FGFR3 alterations; and (b) administering an FGFR inhibitor, in particular at a dose of about 8 mg per day, in particular erdafitinib, more in particular erdafitinib at a dose of about 8 mg per day, at a dose of about 8 mg per day to the patient if one or more FGFR gene alterations is present in the sample.

Also described herein are methods of treating HR-NMIBC comprising (a) evaluating a biological sample from a patient that has been diagnosed with HR-NMIBC for the presence of one or more FGFR gene alterations, in particular one or more FGFR2 or FGFR3 alterations; and (b) administering an FGFR inhibitor, in particular at a dose of about 6 mg per day, in particular erdafitinib, more in particular erdafitinib at a dose of about 6 mg per day, at a dose of about 6 mg per day to the patient if one or more FGFR gene alterations is present in the sample.

Also described herein are methods of treating IR-NMIBC comprising (a) evaluating a biological sample from a patient that has been diagnosed with IR-NMIBC for the presence of one or more FGFR gene alterations, in particular one or more FGFR2 or FGFR3 alterations; and (b) administering an FGFR inhibitor, in particular at a dose of about 8 mg per day, in particular erdafitinib, more in particular erdafitinib at a dose of about 8 mg per day, to the patient if one or more FGFR gene alterations is present in the sample.

Also described herein are methods of treating IR-NMIBC comprising (a) evaluating a biological sample from a patient that has been diagnosed with IR-NMIBC for the presence of one or more FGFR gene alterations, in particular one or more FGFR2 or FGFR3 alterations; and (b) administering an FGFR inhibitor, in particular at a dose of about 6 mg per day, in particular erdafitinib, more in particular erdafitinib at a dose of about 6 mg per day, to the patient if one or more FGFR gene alterations is present in the sample.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with HR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor, in particular at a dose of about 6 mg per day, in particular erdafitinib, more in particular erdafitinib at a dose of about 6 mg per day, for the manufacture of a medicament for the treatment of a patient that has been diagnosed with HR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day; and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day; and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with IR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor, in particular at a dose of about 6 mg per day, in particular erdafitinib, more in particular erdafitinib at a dose of about 6 mg per day, for the manufacture of a medicament for the treatment of a patient that has been diagnosed with IR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day, and wherein the FGFR inhibitor, in particular erdafitinib, is administered or is to be administered after evaluation of a biological sample from the patient for the presence of one or more FGFR2 or FGFR3 gene alterations and if one or more FGFR2 or FGFR3 gene alterations is present in the sample.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or FGFR3 gene alterations is present in the sample.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or FGFR3 gene alterations is present in the sample.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or FGFR3 gene alterations is present in the sample.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or FGFR3 gene alterations is present in the sample.

Further provided herein are methods of treating intermediate risk non-muscle invasive bladder cancer (IR-NMIBC) comprising, consisting of, or consisting essentially of, for example, administering an FGFR inhibitor at a dose of about 8 mg per day to a patient that has been diagnosed with IR-NMIBC who harbors at least one FGFR2 genetic alteration and/or FGFR3 genetic alteration. In certain embodiments, the patient has a papillary tumor. In some embodiments, the patient has an incomplete transurethral resection. In further embodiments, the patient exhibits a complete response to the FGFR inhibitor at about 3 months.

Further provided herein are methods of treating intermediate risk non-muscle invasive bladder cancer (IR-NMIBC) comprising, consisting of, or consisting essentially of, for example, administering an FGFR inhibitor at a dose of about 6 mg per day to a patient that has been diagnosed with IR-NMIBC who harbors at least one FGFR2 genetic alteration and/or FGFR3 genetic alteration. In certain embodiments, the patient has a papillary tumor. In some embodiments, the patient has an incomplete transurethral resection. In further embodiments, the patient exhibits a complete response to the FGFR inhibitor at about 3 months.

In certain embodiments, the FGFR2 genetic alteration and/or FGFR3 genetic alteration is an FGFR3 gene mutation, FGFR2 gene fusion, or FGFR3 gene fusion. In some embodiments, the FGFR3 gene mutation is R248C, S249C, G370C, Y373C, or any combination thereof. In still further embodiments, the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof. In certain embodiments, the FGFR inhibitor is erdafitinib.

BRIEF DESCRIPTION OF THE DRAWINGS

The summary, as well as the following detailed description, is further understood when read in conjunction with the appended drawings. For the purpose of illustrating the disclosed methods or uses, the drawings show exemplary embodiments of the methods or uses; however, the methods or uses are not limited to the specific embodiments disclosed. In the drawings.

DETAILED DESCRIPTION OF ILLUSTRATIVE EMBODIMENTS

Figure 1:
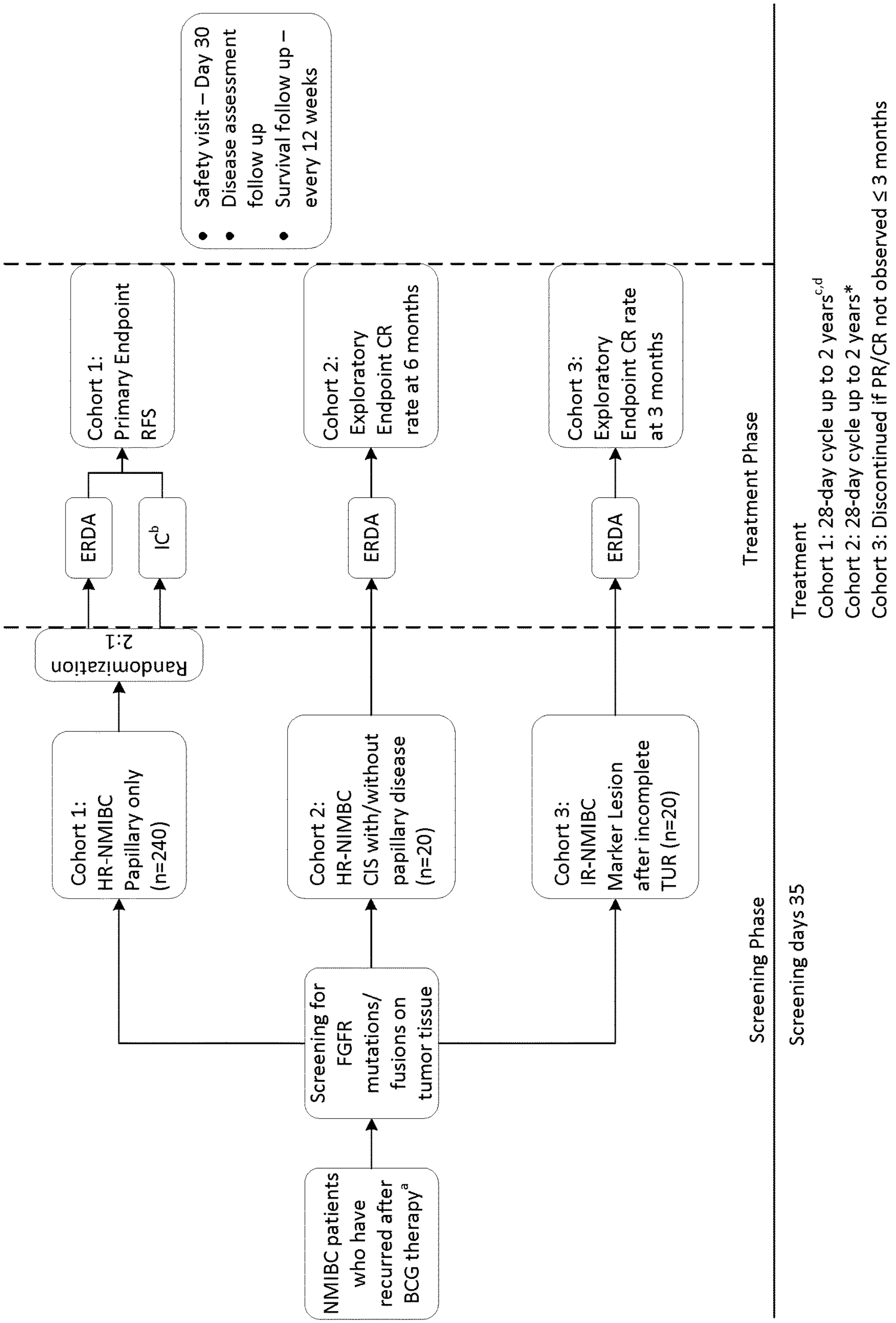
FIG. 1 represents the study scheme for the phase 2, multicenter, open-label study to evaluate the safety and efficacy of erdafitinib in subjects with HR-NMIBC harboring select FGFR genetic alterations (FGFR translocations or mutations), who recurred after BCG therapy. The footnote (a) denotes investigator's choice of intravesical—Gemcitabine/mitomycin C (MMC)/Hyperthermic MMC therapy. The footnote (b) signifies a 28-day cycle up to two years until the patient has disease recurrence or progression, intolerable toxicity, withdraws consent. The footnote (c) signifies a 28-day cycle up to two years in patients in Cohort 1 with confirmed high-grade recurrence on investigator's choice who may cross over to treatment with erdafitinib. The footnote (d) signifies up to six-months treatment, but discontinuation if a CR is not observed in less than or equal to three months. As used in FIG. 1, BCG stands for Bacillus Calmette-Guerin; CIS stands for carcinoma in situ; CR stands for complete response; ERDA stands for erdafitinib; FGFR stands for fibroblast growth factor receptor; HR stands for high-risk; IC stands for intravesical chemotherapy; IR stands for intermediate-risk; MMC stands for mitomycin C; NMIBC stands for non-muscle-invasive bladder cancer; RFS stands for recurrence-free survival; and TUR stands for transurethral resection.
Figure 2:
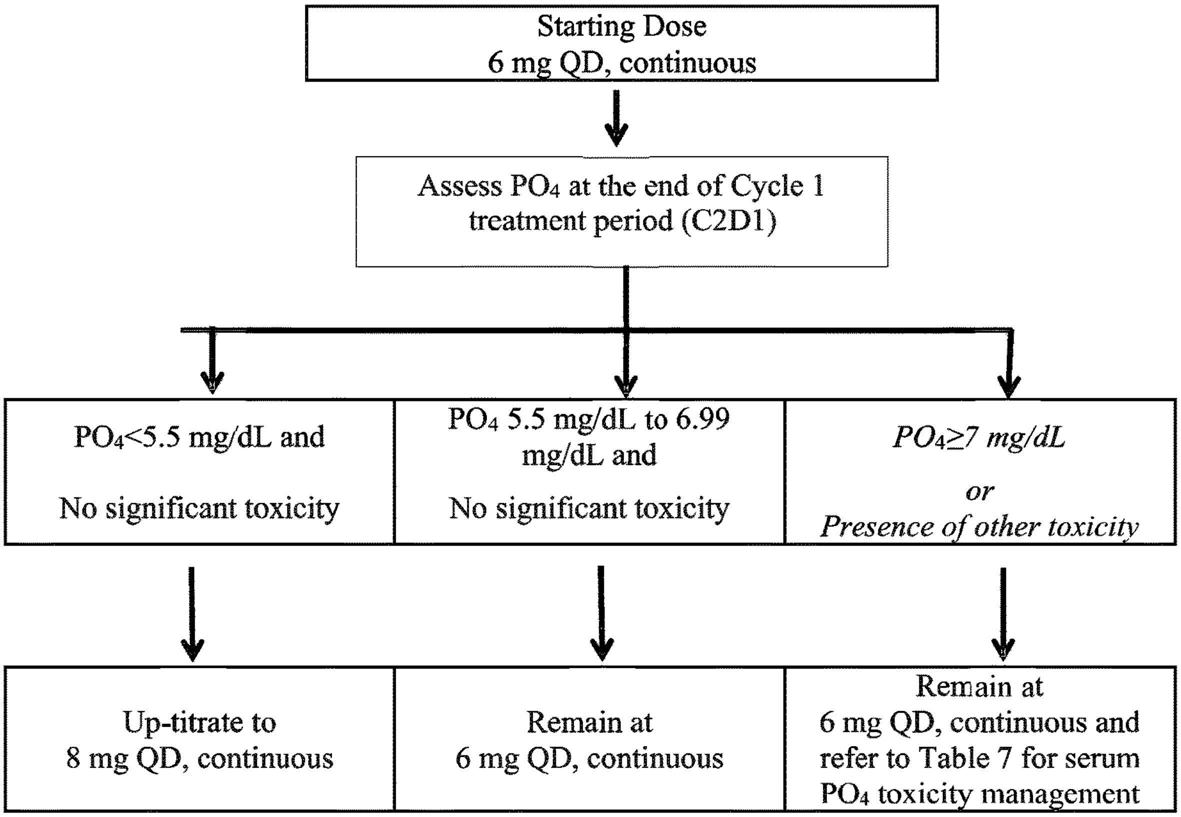
FIG. 2 represents the dose titration of erdafitinib from 6 mg to 8 mg daily regimen.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Certain Terminology

The transitional terms "comprising", "consisting essentially of", and "consisting" are intended to connote their generally in accepted meanings in the patent vernacular; that is, (i) "comprising", which is synonymous with "including", "containing", or "characterized by", is inclusive or open-ended and does not exclude additional, unrecited elements or method steps; (ii) "consisting of" excludes any element, step, or ingredient not specified in the claim; and (iii) "consisting essentially of" limits the scope of a claim or embodiment to the specified materials or steps "and those that do not materially affect the basic and novel characteristic(s)" of the claimed invention or the embodiment. More specifically, the basic and novel characteristics relates to the ability of the method or use to provide at least one of the benefits described herein, including but not limited to the ability to improve the survivability of the human population relative to the survivability of the comparative human population described elsewhere herein. Embodiments described in terms of the phrase "comprising" (or its equivalents), also provide, as embodiments, those which are independently described in terms of "consisting of" and "consisting essentially of".

When a value is expressed as an approximation by use of the descriptor "about", it will be understood that the particular value forms another embodiment. If not otherwise specified, the term "about" signifies a variance of 10% of the associated value, but additional embodiments include those where the variance may be ±5%, ±15%, ±20%, ±25%, or ±50%, in particular the term "about" signifies a variance of ±5% or ±10% of the associated value, more in particular ±5%.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used herein, the singular forms "a," "an," and "the" include the plural.

The following abbreviations are used throughout the disclosure: FGFR (fibroblast growth factor receptor); FGFR3-TACC3 V1 (fusion between genes encoding FGFR3 and transforming acidic coiled-coil containing protein 3 variant 1); FGFR3-TACC3 V3 (fusion between genes encoding FGFR3 and transforming acidic coiled-coil containing protein 3 variant 3); FGFR3-BAIAP2L1 (fusion between genes encoding FGFR3 and brain-specific angiogenesis inhibitor 1-associated protein 2-like protein 1); FGFR2-BICC1 (fusion between genes encoding FGFR2 and bicaudal C homolog 1); FGFR2-CASP7 (fusion between genes encoding FGFR2 and caspase 7).

As used herein, "patient" is intended to mean any animal, in particular, mammals. Thus, the methods or uses are applicable to human and nonhuman animals, although most preferably with humans. The terms "patient" and "subject" and "human" may be used interchangeably.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

The term "dosage" refers to the information of the amount of the therapeutic to be taken by the subject and the frequency of the number of times the therapeutic is to be taken by the subject.

The term "dose" refers to the amount or quantity of the therapeutic to be taken each time.

The term "cancer" as used herein refers to an abnormal growth of cells which tend to proliferate in an uncontrolled way and, in some cases, to metastasize (spread).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., erdafitinib and a co-agent, are both administered to a patient simultaneously in the form of a single unit or single dosage form. The term "non-fixed combination" means that the active ingredients, e.g., erdafitinib and a co-agent, are administered to a patient as separate units or separate dosage forms, either simultaneously, concurrently or sequentially with no specific intervening time limits, wherein such administration provides safe and effective levels of the two active ingredients in the body of the human. The latter also applies to cocktail therapy, e.g., the administration of three or more active ingredients.

The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The term "recurrence-free survival" (RSF) is defined as the time from the date of randomization until the date of the reappearance of high-risk disease (high-grade Ta, T1 or CIS), or death, whichever is reported first. Patients who are recurrence-free and alive or have unknown status will be censored at the last tumor assessment. RFS will be assessed by central histopathologic review.

The term "recurrence-free survival 2" (RFS2) is defined as the time from the date of randomization until the date of the reappearance of high-risk disease on the first subsequent non-surgical anticancer treatment, or death, whichever is reported first. Participants who are recurrence-free and alive or have unknown status will be censored at the last tumor assessment.

The term "time to progression" is defined as the time from the date of randomization until the date of first documented evidence of any of progression or death. Patients who are progression-free and alive or have unknown status will be censored at the date of the last tumor assessment.

The term "time to disease worsening" is defined as the time from the date of randomization to the date of first documented evidence of change in therapy indicative of more advanced disease. Patients who are free of disease worsening and alive or have unknown status will be censored at the last tumor assessment.

The term "time to disease worsening" may also be defined as the time from the date of randomization to the date of first documented evidence of cystectomy, change in therapy indicative of more advanced disease (including systemic chemotherapy or radiotherapy). Patients who are free of disease worsening and alive or have unknown status will be censored at the last tumor assessment.

The term "disease-specific survival" is defined as the time from the date of randomization to the date of the participant's death resulting from bladder cancer. Patients who are alive or have unknown vital status will be censored at the date the participant was last known to be alive. Participants whose death result from causes other than bladder cancer will be censored at their death dates.

The term "overall survival" (OS) is defined as the time from the date of randomization to the date of the participant's death resulting from any cause. Patients who are alive or have unknown vital status will be censored at the date the participant was last known to be alive.

The term "complete response" (CR) is defined as disappearance of marker lesion, with no remnant present and no viable tumor seen on histopathological examination.

The term "partial response" (PR) is defined as at least a 30% decrease in the sum of diameters of target lesions, taking as reference the baseline sum diameters.

The term "adverse event" is any untoward medical event that occurs in a participant administered an investigational product, and it does not necessarily indicate only events with clear causal relationship with the relevant investigational product.

The term "placebo" as used herein means administration of a pharmaceutical composition that does not include an FGFR inhibitor.

The term "randomization" as it refers to a clinical trial refers to the time when the patient is confirmed eligible for the clinical trial and gets assigned to a treatment arm.

The terms "kit" and "article of manufacture" are used as synonyms.

"Biological samples" refers to any sample for a patient in which cancerous cells can be obtained and detection of a FGFR genetic alteration is possible. Suitable biological samples include, but are not limited to, blood, lymph fluid, bone marrow, a solid tumor sample, or any combination thereof. In some embodiments, the biological sample can be formalin-fixed paraffin-embedded tissue (FFPET).

"Cmax" is the maximum observed analyze concentration.

"Tmax" is the actual sampling time to reach maximum observed analyte concentration.

"AUClast" is time zero to the time of the last measurable (non-below quantification limit [BQL]) analyte concentration.

"AUCinfinity" is time zero to infinite time

FGFR Genetic Alterations

Described herein are methods of or uses for treating HR-NMIBC comprising, consisting of, or consisting essentially of administering an FGFR inhibitor at a dose of about 8 mg per day to a patient that has been diagnosed with HR-NMIBC and harbors at least one FGFR2 genetic alteration and/or FGFR3 genetic alteration (i.e., one or more FGFR2 genetic alterations, one or more FGFR3 genetic alterations, or a combination thereof). Also described herein are methods of or uses for treating HR-NMIBC comprising, consisting of, or consisting essentially of administering at least one fibroblast growth factor receptor (FGFR) inhibitor at a dose of about 8 mg per day to a patient that has been diagnosed with HR-NMIBC and harbors at least one FGFR2 genetic alteration and/or FGFR3 genetic alteration. Further described herein are methods of or uses for treating HR-NMIBC comprising, consisting of, or consisting essentially of administering two or more fibroblast growth factor receptor (FGFR) inhibitor at a dose of about 8 mg per day to a patient that has been diagnosed with HR-NMIBC and harbors at least one FGFR2 genetic alteration and/or FGFR3 genetic alteration. The same method of treatment embodiments apply for the uses described herein. In an embodiment, in the methods of or uses for treating HR-NMIBC, the FGFR inhibitor is administered or is to be administered at a dose of about 6 mg per day. In an embodiment, the FGFR inhibitor is erdafitinib.

Described herein are methods of or uses for treating IR-NMIBC comprising, consisting of, or consisting essentially of administering an FGFR inhibitor at a dose of about 8 mg per day to a patient that has been diagnosed with IR-NMIBC and harbors at least one FGFR2 genetic alteration and/or FGFR3 genetic alteration (i.e., one or more FGFR2 genetic alterations, one or more FGFR3 genetic alterations, or a combination thereof). Also described herein are methods of or uses for treating IR-NMIBC comprising, consisting of, or consisting essentially of administering at least one fibroblast growth factor receptor (FGFR) inhibitor at a dose of about 8 mg per day to a patient that has been diagnosed with IR-NMIBC and harbors at least one FGFR2 genetic alteration and/or FGFR3 genetic alteration. Further described herein are methods of or uses for treating IR-NMIBC comprising, consisting of, or consisting essentially of administering two or more fibroblast growth factor receptor (FGFR) inhibitor at a dose of about 8 mg per day to a patient that has been diagnosed with IR-NMIBC and harbors at least one FGFR2 genetic alteration and/or FGFR3 genetic alteration. The same method of treatment embodiments apply for the uses described herein. In an embodiment, in the methods of or uses for treating IR-NMIBC, the FGFR inhibitor is administered or is to be administered at a dose of about 6 mg per day. In an embodiment, the FGFR inhibitor is erdafitinib.

The fibroblast growth factor (FGF) family of protein tyrosine kinase (PTK) receptors regulates a diverse array of physiologic functions including mitogenesis, wound healing, cell differentiation and angiogenesis, and development.

Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state.

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Knights et al., *Pharmacology and Therapeutics* 2010 125:1 (105-117); Korc M. et al *Current Cancer Drug Targets* 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

In certain embodiments, the HR-NMIBC or IR-NMIBC is susceptible to an FGFR2 genetic alteration and/or an FGFR3 genetic alteration.

As used herein, "FGFR genetic alteration" refers to an alteration in the wild type FGFR gene, including, but not limited to, FGFR fusion genes, FGFR mutations, FGFR amplifications, or any combination thereof. The terms "variant" and "alteration" are used interchangeably herein.

In certain embodiments, the FGFR2 or FGFR3 genetic alteration is an FGFR gene fusion. "FGFR fusion" or "FGFR gene fusion" refers to a gene encoding a portion of FGFR (e.g., FGRF2 or FGFR3) and one of the herein disclosed fusion partners, or a portion thereof, created by a translocation between the two genes. The terms "fusion" and "translocation" are used interchangeable herein. The presence of one or more of the following FGFR fusion genes in a biological sample from a patient can be determined using the disclosed methods or uses or by methods known to those of ordinary skill in the art: FGFR3-TACC3, FGFR3-BAIAP2L1, FGFR2-BICC1, FGFR2-CASP7, or any combination thereof. In certain embodiments, FGFR3-TACC3 is FGFR3-TACC3 variant 1 (FGFR3-TACC3 V1) or FGFR3-TACC3 variant 3 (FGFR3-TACC3 V3). Table 1 provides the FGFR fusion genes and the FGFR and fusion partner exons that are fused. The sequences of the individual FGFR fusion genes are disclosed in Table 4.

TABLE 1

| Fusion Gene | FGFR Exon | Partner Exon |
|---|---|---|
| FGFR2 | | |
| FGFR2-BICC1 | 19 | 3 |
| FGFR2-CASP7 | 19 | 4 |
| FGFR3 | | |
| FGFR3-BAIAP2L1 | 18 | 2 |
| FGFR3-TACC3 V1 | 18 | 11 |
| FGFR3-TACC3 V3 | 18 | 10 |

FGFR genetic alterations include FGFR single nucleotide polymorphism (SNP). "FGFR single nucleotide polymorphism" (SNP) refers to a FGFR2 or FGFR3 gene in which a single nucleotide differs among individuals. In certain embodiments, the FGFR2 or FGFR3 genetic alteration is an FGFR3 gene mutation. In particular, FGFR single nucleotide polymorphism" (SNP) refers to a FGFR3 gene in which a single nucleotide differs among individuals. The presence of one or more of the following FGFR SNPs in a biological sample from a patient can be determined by methods known to those of ordinary skill in the art or methods disclosed in WO 2016/048833, FGFR3 R248C, FGFR3 S249C, FGFR3 G370C, FGFR3 Y373C, or any combination thereof. The sequences of the FGFR SNPs are provided in Table 2.

TABLE 2

| FGFR3 mutant | Sequence |
|---|---|
| FGFR3 R248C | TCGGACCGCGGCAACTACACCTGCGTCGTGGAGAACAAGTTTGGCAGCA<br>TCCGGCAGACGTACACGCTGGACGTGCTGGAG(**T**)GCTCCCCGCACCGGC<br>CCATCCTGCAGGCGGGGCTGCCGGCCAACCAGACGGCGGTGCTGGGCAG<br>CGACGTGGAGTTCCACTGCAAGGTGTACAGTGACGCACAGCCCCACATC<br>CAGTGGCTCAAGCACGTGGAGGTGAATGGCAGCAAGGTGGGCCCGGACG<br>GCACACCCTACGTTACCGTGCTCA<br>(SEQ ID NO: 1) |
| FGFR3 S249C | GACCGCGGCAACTACACCTGCGTCGTGGAGAACAAGTTTGGCAGCATCC<br>GGCAGACGTACACGCTGGACGTGCTGGGTGAGGGCCCTGGGGCGGCGCG<br>GGGGTGGGGGCGGCAGTGGCGGTGGTGGTGAGGGAGGGGGTGGCCCCT<br>GAGCGTCATCTGCCCCCACAGAGCGCT(**G**)CCCGCACCGGCCCATCCTGCA<br>GGCGGGGCTGCCGGCCAACCAGACGGCGGTGCTGGGCAGCGACGTGGAG<br>TTCCACTGCAAGGTGTACAGTGACGCACAGCCCCACATCCAGTGGCTCAA<br>GCACGTGGAGGTGAATGGCAGCAAGGTGGGCCCGGACGGCACACCCTAC<br>GTTACCGTGCTCAAGGTGGGCCACCGTGTGCACGT<br>(SEQ ID NO: 2) |
| FGFR3 G370C | GCGGGCAATTCTATTGGGTTTTCTCATCACTCTGCGTGGCTGGTGGTGCT<br>GCCAGCCGAGGAGGAGCTGGTGGAGGCTGACGAGGCG(**T**)GCAGTGTGTA<br>TGCAGGCATCCTCAGCTACGGGGTGGGCTTCTTCCTGTTCATCCTGGTGG<br>TGGCGGCTGTGACGCTCTGCCGCCTGCGCAGCCCCCCCAAGAAAGGCCT<br>GGGCTCCCCCACCGTGCACAAGATCTCCCGCTTCCCG<br>(SEQ ID NO: 3) |

TABLE 2-continued

| FGFR3 mutant | Sequence |
|---|---|
| FGFR3 Y373C* | CTAGAGGTTCTCTCCTTGCACAACGTCACCTTTGAGGACGCCGGGGAGTA CACCTGCCTGGCGGGCAATTCTATTGGGTTTTCTCATCACTCTGCGTGGCT GGTGGTGCTGCCAGCCGAGGAGGAGCTGGTGGAGGCTGACGAGGCGGGC AGTGTGT(**G**)TGCAGGCATCCTCAGCTACGGGGTGGGCTTCTTCCTGTTCA TCCTGGTGGTGGCGGCTGTGACGCTCTGCCGCCTGCGCAGCCCCCCCAAG AAAGGCCTGGGCTCCCCCACCGTGCACAAGATCTCCCGCTTCCCGCTCAA GC (SEQ ID NO:4) |

Sequences correspond to nucleotides 920-1510 of FGFR3 (Genebank ID # NM_000142.4).
Nucleotides in bold underline represent the SNP.
*Sometimes mistakenly referred to as Y375C in the literature.

As used herein, "FGFR genetic alteration gene panel" includes one or more of the above listed FGFR genetic alterations. In some embodiments, the FGFR genetic alteration gene panel is dependent upon the patient's cancer type.

The FGFR genetic alteration gene panel that is used in the evaluating step of the disclosed methods is based, in part, on the patient's cancer type. For patients with HR-NMIBC or IR-NMIBC, a suitable FGFR genetic alteration gene panel can comprise FGFR3-TACC3 Vl, FGFR3-TACC3 V3, FGFR3-BAIAP2L1, FGFR2-BICC1, FGFR2-CASP7, FGFR3 R248C, FGFR3 S249C, FGFR3 G370C, or FGFR3 Y373C, or any combination thereof.

FGFR Inhibitors for Use in the Disclosed Methods or Uses

Suitable FGFR inhibitors for use in the disclosed methods or uses are provided herein. The FGFR inhibitors may be used alone or in combination for the treatment methods described herein.

In some embodiments, if one or more FGFR genetic alterations are present in the sample, the HR-NMIBC or IR-NMIBC can be treated with a FGFR inhibitor disclosed in U.S. Publication No. 2013/0072457 A1 (incorporated herein by reference), including any tautomeric or stereochemically isomeric form thereof, and a N-oxide thereof, a pharmaceutically acceptable salt thereof, or a solvate thereof.

In some aspects, for example, the HR-NMIBC or IR-NMIBC may be treated with N-(3,5-dimethoxyphenyl)-N'-(1-methylethyl)-N-[3-(1-methyl-1H-pyrazol-4-yl)quinoxalin-6-yl]ethane-1,2-diamine (referred to herein as "JNJ-42756493" or "JNJ493" or erdafitinib), including any tautomeric form thereof, N-oxides thereof, pharmaceutically acceptable salts thereof, or solvates thereof. In some embodiments, the FGFR inhibitor can be the compound of formula (I), also referred to as erdafitinib:

(I)

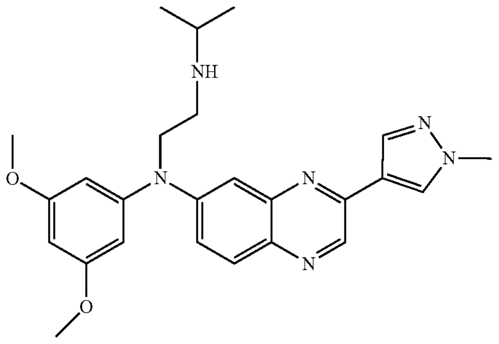

or a pharmaceutically acceptable salt thereof. In some aspects, the pharmaceutically acceptable salt is a HCl salt. In preferred aspects, erdafitinib base is used.

Erdafitinib (also referred to as ERDA), a once-daily oral pan-FGFR kinase inhibitor, has been approved by the U.S. Food and Drug Administration (FDA) for the treatment of adult patients who have locally advanced UC or mUC which has susceptible FGFR3 or FGFR2 genetic alterations and who have progressed during or following at least one line of prior platinum-containing chemotherapy, including within 12 months of neoadjuvant or adjuvant platinum-containing chemotherapy. Loriot Y et al. *NEJM.* 2019; 381:338-48. Erdafitinib has shown clinical benefits and tolerability in patients with mUC and alteration in FGFR expressions. Tabernero J, et al. *J Clin Oncol.* 2015; 33:3401-3408; Soria J-C, et al. *Ann Oncol.* 2016; 27(Suppl 6):vi266-vi295. Abstract 781PD; Siefker-Radtke A O, et al. ASCO 2018. Abstract 4503; Siefker-Radtke A, et al. ASCO-GU 2018. Abstract 450.

In some embodiments, the HR-NMIBC or IR-NMIBC can be treated with a FGFR inhibitor wherein the FGFR inhibitor is N-[5-[2-(3,5-Dimethoxyphenyl)ethyl]-2H-pyrazol-3-yl]-4-(3,5-diemthylpiperazin-1-yl)benzamide (AZD4547), as described in Gavine, P. R., et al., AZD4547: An Orally Bioavailable, Potent, and Selective Inhibitor of the Fibroblast Growth Factor Receptor Tyrosine Kinase Family, Cancer Res. Apr. 15, 2012 72; 2045:

(II)

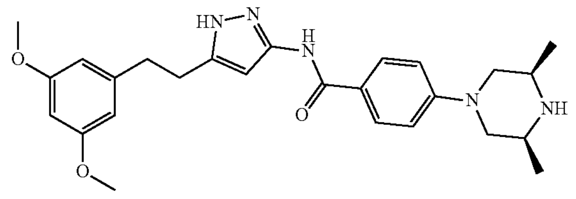

including, when chemically possible, any tautomeric or stereochemically isomeric form thereof, and a N-oxide thereof, a pharmaceutically acceptable salt thereof, or a solvate thereof.

In some embodiments, the HR-NMIBC or IR-NMIBC can be treated with a FGFR inhibitor wherein the FGFR inhibitor is 3-(2,6-Dichloro-3,5-dimethoxy-phenyl)-1-{6-[4-(4 ethyl-piperazin-1-yl)-phenylamino]-pyrimid-4-yl}-methyl-urea (NVP-BGJ398) as described in Int'l Publ. No. WO2006/000420:

(III)

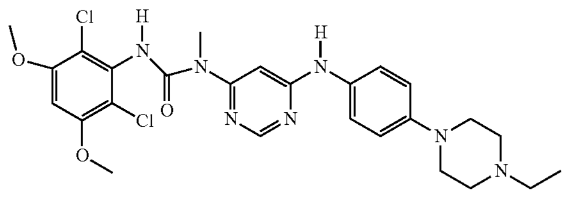

including, when chemically possible, any tautomeric or stereochemically isomeric form thereof, and a N-oxide thereof, a pharmaceutically acceptable salt thereof, or a solvate thereof.

In some embodiments, the HR-NMIBC or IR-NMIBC can be treated with a FGFR inhibitor wherein the FGFR inhibitor is 4-amino-5-fluoro-3-[6-(4-methylpiperazin-1-yl)-1H-benzimidazol-2-yl]-1H-quinolin-2-one (dovitinib) as described in Int'l Publ. No. WO2006/127926:

(IV)

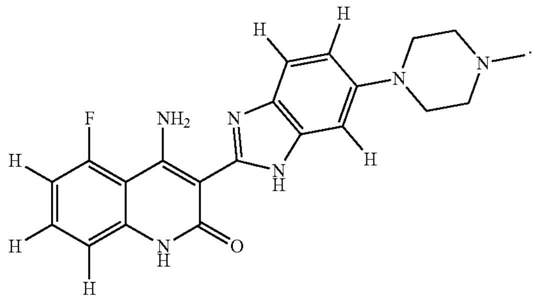

including, when chemically possible, any tautomeric or stereochemically isomeric form thereof, and a N-oxide thereof, a pharmaceutically acceptable salt thereof, or a solvate thereof.

In some embodiments, the HR-NMIBC or IR-NMIBC can be treated with a FGFR inhibitor wherein the FGFR inhibitor is 6-(7-((1-Aminocyclopropyl)-methoxy)-6-methoxyquinolin-4-yloxy)-N-methyl-1-naphthamide (AL3810) (lucitanib; E-3810), as described in Bello, E. et al., E-3810 Is a Potent Dual Inhibitor of VEGFR and FGFR that Exerts Antitumor Activity in Multiple Preclinical Models, Cancer Res Feb. 15, 2011 71(A)1396-1405 and Int'l Publ. No. WO2008/112408:

(V)

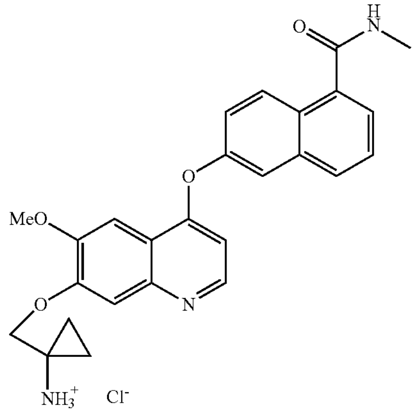

including, when chemically possible, any tautomeric or stereochemically isomeric form thereof, and a N-oxide thereof, a pharmaceutically acceptable salt thereof, or a solvate thereof.

In some embodiments, the HR-NMIBC or IR-NMIBC can be treated with a FGFR inhibitor wherein the FGFR inhibitor is pemigatinib (11-(2,6-difluoro-3,5-dimethoxyphenyl)-13-ethyl-4-(morpholin-4-ylmethyl)-5,7,11,13-tetrazatricyclo[7.4.$0^{2,6}$]trideca-1,3,6,8-tetraen-12-one:

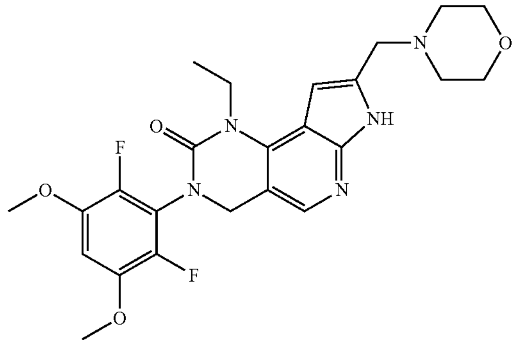 [SMILES: CCN1C(=O)N(c2c(F)c(OC)cc(OC)c2F)Cc2cnc3[nH]c(CN4CCOCC4)cc3c21]

including, when chemically possible, any tautomeric or stereochemically isomeric form thereof, and a N-oxide thereof, a pharmaceutically acceptable salt thereof, or a solvate thereof.

Additional suitable FGFR inhibitors include BAY1163877 (Bayer), BAY1179470 (Bayer), TAS-120 (Taiho), ARQ087 (ArQule), ASP5878 (Astellas), FF284 (Chugai), FP-1039 (GSK/FivePrime), Blueprint, LY-2874455 (Lilly), RG-7444 (Roche), or any combination thereof, including, when chemically possible, any tautomeric or stereochemical isomeric forms thereof, N-oxides thereof, pharmaceutically acceptable salts thereof, or solvates thereof.

In an embodiment the FGFR inhibitor generally, and erdafitinib more specifically, is administered as a pharmaceutically acceptable salt. In a preferred embodiment the FGFR inhibitor generally, and erdafitinib more specifically, is administered in base form. In an embodiment the FGFR inhibitor generally, and erdafitinib more specifically, is administered as a pharmaceutically acceptable salt in an amount corresponding to 8 mg base equivalent or corresponding to 9 mg base equivalent. In an embodiment the FGFR inhibitor generally, and erdafitinib more specifically, is administered as a pharmaceutically acceptable salt in an amount corresponding to 6 mg base equivalent. In an embodiment the FGFR inhibitor generally, and erdafitinib more specifically, is administered in base form in an amount of 8 mg or 9 mg. In an embodiment the FGFR inhibitor generally, and erdafitinib more specifically, is administered in base form in an amount of 6 mg.

The salts can be prepared by for instance reacting the FGFR inhibitor generally, and erdafitinib more specifically, with an appropriate acid in an appropriate solvent.

Acid addition salts may be formed with acids, both inorganic and organic. Examples of acid addition salts include salts formed with an acid selected from the group consisting of acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

In an embodiment, the FGFR inhibitor generally, and erdafitinib more specifically, is administered in the form of a solvate. As used herein, the term "solvate" means a physical association of erdafitinib with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of solvents that may form solvates include water, isopropanol, ethanol, methanol, DMSO, ethyl acetate, acetic acid or ethanolamine and the like.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid-State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallization conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals).

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or nonradioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

Methods of Treatment and Uses

Described herein are methods of treating HR-NMIBC comprising, consisting of, or consisting essentially of administering an FGFR inhibitor at a dose of about 8 mg per day to a patient that has been diagnosed with HR-NMIBC who harbors at least one FGFR2 genetic alteration and/or FGFR3 genetic alteration.

Described herein are methods of treating HR-NMIBC comprising, consisting of, or consisting essentially of administering an FGFR inhibitor at a dose of about 6 mg per day to a patient that has been diagnosed with HR-NMIBC who harbors at least one FGFR2 genetic alteration and/or FGFR3 genetic alteration.

Further provided herein are methods of treating IR-NMIBC comprising, consisting of, or consisting essential of, administering an FGFR inhibitor at a dose of about 8 mg per day to a patient that has been diagnosed with IR-NMIBC who harbors at least one FGFR2 genetic alteration and/or FGFR3 genetic alteration.

Further provided herein are methods of treating IR-NMIBC comprising, consisting of, or consisting essential of, administering an FGFR inhibitor at a dose of about 6 mg per day to a patient that has been diagnosed with IR-NMIBC who harbors at least one FGFR2 genetic alteration and/or FGFR3 genetic alteration.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with HR-NMIBC who harbors at least one FGFR2 genetic alteration and/or FGFR3 genetic alteration.

Described herein is the use of an FGFR inhibitor, in particular at a dose of about 6 mg per day, in particular erdafitinib, more in particular erdafitinib at a dose of about 6 mg per day, for the manufacture of a medicament for the treatment of a patient that has been diagnosed with HR-NMIBC who harbors at least one FGFR2 genetic alteration and/or FGFR3 genetic alteration.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day.

Described herein is the use of an FGFR inhibitor, in particular at a dose of about 8 mg per day, in particular erdafitinib, more in particular erdafitinib at a dose of about 8 mg per day, for the manufacture of a medicament for the treatment of a patient that has been diagnosed with IR-NMIBC who harbors at least one FGFR2 genetic alteration and/or FGFR3 genetic alteration.

Described herein is the use of an FGFR inhibitor, in particular at a dose of about 6 mg per day, in particular erdafitinib, more in particular erdafitinib at a dose of about 6 mg per day, for the manufacture of a medicament for the treatment of a patient that has been diagnosed with IR-NMIBC who harbors at least one FGFR2 genetic alteration and/or FGFR3 genetic alteration.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 6 mg per day.

Said methods and uses also encompass administration of at least one, one, two, three or four FGFR inhibitors to a patient that has been diagnosed with HR-NHIMB or IR-NMIBC.

In certain embodiments, the patient received at least one therapy prior to administration of said FGFR inhibitor. In further embodiments, patient received BCG therapy prior to said administration of said FGFR inhibitor.

In some embodiments, the BCG therapy is adequate BCG therapy. The minimum requirements for adequate BCG therapy include (1) at least 5 of 6 full doses of an initial induction course plus at least 1 maintenance (2 of 3 full weekly doses) in a 6-month period, or (2) at least 5 of 6 full doses of an initial induction course plus at least 2 of 6 full doses of a second induction course. A full dose of BCG comprises 1 full vial with a minimum of $1\times10^8$ colony forming units (CFU).

In some embodiments, the patient is unresponsive to BCG therapy. A patient is unresponsive to BCG therapy if the patient has one of the following recurrence disease status and if the patient received adequate BCG therapy. The recurrence disease status are: (1) persistent or recurrent carcinoma in situ (CIS) alone or with recurrent Ta/T1 (noninvasive papillary disease/tumor invades the subepithelial connective tissue) disease within 12 months of completion of adequate BCG therapy, (2) recurrent high-grade Ta/T1 disease within 6 months of completion of adequate BCG therapy, or (3) T1 high-grade at the first disease assessment following an induction of BCG course.

In still further embodiments, the patient is BCG experienced. A patient is BCG experienced if the patient has recurrent high-grade Ta/T1 disease within 12 months of completion of BCG therapy and their prior BCG therapy is the minimum treatment requirement. The minimum treatment requirement is: (1) at least 5 of 6 full doses of an initial induction course; and (2) at least 5 of 6 full doses of an initial induction course plus at least 1 maintenance (2 of 3 weekly doses) in a 6-month period. One-half dose or one-third dose is allowed during maintenance.

In certain embodiments, the patient has a papillary tumor. Papillary tumors may grow from tissue that lines the inside of an organ, and may occur in the bladder, thyroid and breast.

In further embodiments, the patient has carcinoma in situ. In certain embodiments, the carcinoma in situ refers to a group of abnormal cells that remain in the place where they first formed. In certain embodiments, the patient has stage 0 disease.

In some embodiments, the patient did not previously receive or is ineligible for a cystectomy, i.e. surgery to remove all or part of the bladder or to remove a cyst in the body.

The determination of eligibility may be made, for example, by a treating physician.

In some embodiments, the patient has an incomplete transurethral resection, e.g. a surgery to remove tissue with a special instrument inserted through the urethra.

In certain embodiments, said administration of the FGFR inhibitor provides an increase in RFS, time to progression, time to disease worsening, disease-specific survival, OS, RFS rate, RFS2, or CR relative to a patient population with HR-NMIBC or IR-NMIBC that has been administered a placebo. In certain embodiments, said administration of the FGFR inhibitor provides an increase in RFS relative to a patient population with HR-NMIBC or IR-NMIBC that has been administered a placebo. In certain embodiments, said administration of the FGFR inhibitor provides an increase in time to progression relative to a patient population with HR-NMIBC or IR-NMIBC that has been administered a placebo. In certain embodiments, said administration of the FGFR inhibitor provides an increase in time to disease worsening relative to a patient population with HR-NMIBC or IR-NMIBC that has been administered a placebo. In certain embodiments, said administration of the FGFR inhibitor provides an increase in disease-specific survival relative to a patient population with HR-NMIBC or IR-NMIBC that has been administered a placebo. In certain embodiments, said administration of the FGFR inhibitor provides an increase in OS relative to a patient population with HR-NMIBC or IR-NMIBC that has been administered a placebo. In certain embodiments, said administration of the FGFR inhibitor provides an increase in RFS rate relative to a patient population with HR-NMIBC or IR-NMIBC that has been administered a placebo. In certain embodiments, said administration of the FGFR inhibitor provides an increase in RFS2 relative to a patient population with HR-NMIBC or IR-NMIBC that has been administered a placebo. In certain embodiments, said administration of the FGFR inhibitor provides an increase in CR relative to a patient population with HR-NMIBC or IR-NMIBC that has been administered a placebo.

In certain embodiments, the increase in RFS rate is determined at 6 months. In certain embodiments, the increase in RFS rate is determined at 12 months. In certain embodiments, the increase in RFS rate is determined at 24 months.

In certain embodiments, the improvement in anti-tumor activity is relative to treatment with placebo. In certain embodiments, the improvement in anti-tumor activity is relative to no treatment. In certain embodiments, the improvement in anti-tumor activity is relative to standard of care. In certain embodiments, the improvement in anti-tumor activity is relative to investigator's choice. In certain embodiments, the improvement in anti-tumor activity is relative to a patient population with HR-NMIBC or IR-NMIBC that has been administered intravesical gemcitabine. In certain embodiments, the improvement in anti-tumor activity is relative to a patient population with HR-NMIBC or IR-NMIBC that has been administered intravesical mitomycin C (MMC)/hyperthermic MMC.

Gemcitabine, which is the active ingredient of gemcitabine hydrochloride (also referred to as GEMZAR®), is a nucleoside metabolic inhibitor that may be administered by intravesical installation, e.g. to the bladder through a urinary catheter. Gemcitabine may be administered as a 200 mg/single use vial or a 1 g/single-use vial. Gemcitabine HCl is 2'-deoxy-2',2'-difluorocytidine monohydrochloride (β-isomer).

Mitomycin C (also referred to as MUTAMYCIN®) is a methylazirinopyrroloindoledione antineoplastic antibiotic isolated from the bacterium *Streptomyces caespitosus* and other *Streptomyces* bacterial species that may be administered by intravesical installation. Intravesical administration of MMC may optionally be hyperthermic, e.g. simultaneous intravesical administration with microwave-induced hyperthermia. To achieve microwave-induced hyperthermia, an applicator may deliver hyperthermia to the bladder wall via direct irradiation.

In some embodiments, the patient exhibits a CR to the FGFR inhibitor at about 6 months. In some embodiments, the patient exhibits a CR to the FGFR inhibitor at about 3 months.

Also provided herein are methods of or uses for improving RFS, time to progression, time to disease worsening, disease-specific survival, OS, RFS rate, RFS2, or CR in a patient that has been diagnosed with HR-NMIBC or IR-NMIBC relative to a patient that has been diagnosed with HR-NMIBC or IR-NMIBC that has not received treatment with an FGFR inhibitor, said method comprising, consisting of, or consisting essential of, administering an FGFR inhibitor, in particular at a dose of about 8 mg per day, or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving RFS in a patient that has been diagnosed with HR-NMIBC relative to a patient that has been diagnosed with HR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving time to progression in a patient that has been diagnosed with HR-NMIBC or IR-NMIBC relative to a patient that has been diagnosed with HR-NMIBC or IR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving time to disease worsening in a patient that has been diagnosed with HR-NMIBC relative to a patient that has been diagnosed with HR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving disease-specific survival in a patient that has been diagnosed with HR-NMIBC or IR-NMIBC relative to a patient that has been diagnosed with HR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC who harbors at least one FGFR2 genetic alteration and/or FGFR3 genetic alteration. In certain embodiments, provided here are methods of or uses for improving OS in a patient that has been diagnosed with HR-NMIBC or IR-NMIBC relative to a patient that has been diagnosed with HR-NMIBC or IR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving RFS rate in a patient that has been diagnosed with HR-NMIBC or IR-NMIBC relative to a patient that has been diagnosed with HR-NMIBC or IR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving RFS2 in a patient that has been diagnosed with HR-NMIBC or IR-NMIBC relative to a patient that has been diagnosed with HR-NMIBC or IR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration. In certain embodiments, provided here are methods of or uses for improving CR in a patient that has been diagnosed with HR-NMIBC or IR-NMIBC relative to a patient that has been diagnosed with HR-NMIBC or IR-NMIBC that has not received treatment with an FGFR inhibitor, said method comprising administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to a patient that has been diagnosed with HR-NMIBC or IR-NMIBC who harbors at least one FGFR2 genetic alteration and/or FGFR3 genetic alteration.

In certain embodiments, the improvement is relative to treatment with placebo. In certain embodiments, the improvement in anti-tumor activity is relative to no treatment. In certain embodiments, the improvement in anti-tumor activity is relative to standard of care. In certain embodiments, the improvement in anti-tumor activity is relative to investigator's choice. In certain embodiments, the improvement in anti-tumor activity is relative to a patient population with HR-NMIBC that has been administered intravesical gemcitabine. In certain embodiments, the improvement in anti-tumor activity is relative to a patient population with HR-NMIBC or IR-NMIBC that has been administered intravesical mitomycin C (MMC)/hyperthermic MMC.

Evaluating a Sample for the Presence of One or More FGFR Genetic Alterations

Also described herein are methods of treating HR-NMIBC comprising, consisting of, or consisting essential of, (a) evaluating a biological sample from a patient that has been diagnosed with HR-NMIBC for the presence of one or more fibroblast growth factor receptor (FGFR) gene alterations; and (b) administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to the patient if one or more FGFR gene alterations is present in the sample.

Also described herein are methods of treating IR-NMIBC comprising (a) evaluating a biological sample from a patient that has been diagnosed with IR-NMIBC for the presence of one or more FGFR gene alterations, in particular one or more FGFR2 or FGFR3 alterations; and (b) administering an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, to the patient if one or more FGFR gene alterations is present in the sample.

Described herein is the use of an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, for the manufacture of a medicament for the treatment of a patient that has been diagnosed with HR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample.

Described herein is the use of an FGFR inhibitor for the manufacture of a medicament for the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day; and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample. In an embodiment, the FGFR inhibitor, in particular erdafitinib, is administered or is to be administered at a dose of about 6 mg per day.

Described herein is the use of an FGFR inhibitor, in particular at a dose of about 8 mg per day or in particular at a dose of about 6 mg per day, in particular erdafitinib, more in particular erdafitinib at a dose of about 8 mg per day or more in particular erdafitinib at a dose of about 6 mg per day, for the manufacture of a medicament for the treatment of a patient that has been diagnosed with IR-NMIBC who harbors at least one FGFR2 genetic alteration and/or FGFR3 genetic alteration, and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample.

Described herein is the use of an FGFR inhibitor for the manufacture of a medicament for the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample. In an embodiment, the FGFR inhibitor, in particular erdafitinib, is administered or is to be administered at a dose of about 6 mg per day.

Described herein is an FGFR inhibitor for use in the treatment of a patient that has been diagnosed with HR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample. In an embodiment, the FGFR inhibitor, in particular erdafitinib, is administered or is to be administered at a dose of about 6 mg per day.

Described herein is an FGFR inhibitor for use in the treatment of a patient that has been diagnosed with IR-NMIBC who harbors at least one FGFR2 genetic alteration and/or FGFR3 genetic alteration, in particular wherein the FGFR inhibitor, in particular erdafitinib, is administered or is to be administered at a dose of about 8 mg per day, and wherein the FGFR inhibitor, in particular erdafitinib, is administered or is to be administered after evaluation of a biological sample from the patient for the presence of one or more FGFR2 or 3 gene alterations and if one or more FGFR2 or 3 gene alterations is present in the sample. In an embodiment, the FGFR inhibitor, in particular erdafitinib, is administered or is to be administered at a dose of about 6 mg per day.

The following methods for evaluating a biological sample for the presence of one or more FGFR genetic alterations apply equally to any of the above disclosed methods of treatment and uses.

The disclosed methods are suitable for treating cancer in a patient if one or more FGFR genetic alterations are present in a biological sample from the patient. In some embodiments, the FGFR genetic alteration can be one or more FGFR fusion genes, in particular one or more FGFR2 or FGFR3 fusion genes. In some embodiments, the FGFR genetic alteration can be one or more FGFR mutations, in particular one or more FGFR3 mutations. In some embodiments, the FGFR genetic alteration can be one or more FGFR amplifications. In some embodiments, a combination of the one or more FGFR genetic alterations can be present in the biological sample from the patient. For example, in some embodiments, the FGFR genetic alterations can be one or more FGFR fusion genes and one or more FGFR mutations. In some embodiments, the FGFR genetic alterations can be one or more FGFR fusion genes and one or more FGFR amplifications. In some embodiments, the FGFR genetic alterations can be one or more FGFR mutations and one or more FGFR amplifications. In yet other embodiments, the FGFR genetic alterations can be one or more FGFR fusion genes, mutations, and amplifications. Exemplary FGFR fusion genes are provided in Table 1 and include but are not limited to: FGFR2-BICC1; FGFR2-CASP7; FGFR3-BAIAP2L1; FGFR3-TACC3 V1; FGFR3-TACC3 V3; or a combination thereof.

Suitable methods for evaluating a biological sample for the presence of one or more FGFR genetic alterations are described in the methods section herein and in WO 2016/048833 and U.S. patent application Ser. No. 16/723,975, which are incorporated herein in their entireties. For example, and without intent to be limiting, evaluating a biological sample for the presence of one or more FGFR genetic alterations can comprise any combination of the following steps: isolating RNA from the biological sample; synthesizing cDNA from the RNA; and amplifying the cDNA (preamplified or non-preamplified). In some embodiments, evaluating a biological sample for the presence of one or more FGFR genetic alterations can comprise: amplifying cDNA from the patient with a pair of primers that bind to and amplify one or more FGFR genetic alterations; and determining whether the one or more FGFR genetic alterations are present in the sample. In some aspects, the cDNA can be pre-amplified. In some aspects, the evaluating step can comprise isolating RNA from the sample, synthesizing cDNA from the isolated RNA, and pre-amplifying the cDNA.

Suitable primer pairs for performing an amplification step include, but are not limited to, those disclosed in WO 2016/048833, as exemplified below in Table 3:

TABLE 3

| Target | Forward Primer | Reverse Primer 5'-3' |
|---|---|---|
| FGFR3-TACC3 V1 | GACCTGGACCGTGTCCTTACC (SEQ ID NO: 5) | CTTCCCCAGTTCCAGGTTCTT (SEQ ID NO: 6) |
| FGFR3-TACC3 V3 | AGGACCTGGACCGTGTCCTT (SEQ ID NO: 7) | TATAGGTCCGGTGGACAGGG (SEQ ID NO: 8) |
| FGFR3-BAIAP2L1 | CTGGACCGTGTCCTTACCGT (SEQ ID NO: 9) | GCAGCCCAGGATTGAACTGT (SEQ ID NO: 10) |
| FGFR2-BICC1 | TGGATCGAATTCTCACTCTCACA (SEQ ID NO: 11) | GCCAAGCAATCTGCGTATTTG (SEQ ID NO: 12) |
| FGFR2-CASP7 | GCTCTTCAATACAGCCCTGATCA (SEQ ID NO: 13) | ACTTGGATCGAATTCTCACTCTCA (SEQ ID NO: 14) |
| FGFR2-CCDC6 | TGGATCGAATTCTCACTCTCACA (SEQ ID NO: 15) | GCAAAGCCTGAATTTTCTTGAATAA (SEQ ID NO: 16) |
| FGFR3 R248C | GCATCCGGCAGACGTACA (SEQ ID NO: 17) | CCCCGCCTGCAGGAT (SEQ ID NO: 18) |
| FGFR3 S249C | GCATCCGGCAGACGTACA (SEQ ID NO: 19) | CCCCGCCTGCAGGAT (SEQ ID NO: 20) |
| FGFR3 G370C | AGGAGCTGGTGGAGGCTGA (SEQ ID NO: 21) | CCGTAGCTGAGGATGCCTG (SEQ ID NO: 22) |
| FGFR3 Y373C | CTGGTGGAGGCTGACGAG (SEQ ID NO: 23) | AGCCCACCCCGTAGCT (SEQ ID NO: 24) |
| FGFR3 R248C | GTCGTGGAGAACAAGTTTGGC (SEQ ID NO: 25) | GTCTGGTTGGCCGGCAG (SEQ ID NO: 26) |

TABLE 3-continued

| Target | Forward Primer | Reverse Primer 5'-3' |
|---|---|---|
| FGFR3 S249C | GTCGTGGAGAACAAGTTTGGC (SEQ ID NO: 27) | GTCTGGTTGGCCGGCAG (SEQ ID NO: 28) |
| FGFR3 G370C | AGGAGCTGGTGGAGGCTGA (SEQ ID NO: 29) | CCGTAGCTGAGGATGCCTG (SEQ ID NO: 30) |
| FGFR3 Y373C | GACGAGGCGGGCAGTG (SEQ ID NO: 31) | GAAGAAGCCCACCCCGTAG (SEQ ID NO: 32) |

The presence of one or more FGFR genetic alterations can be evaluated at any suitable time point including upon diagnosis, following tumor resection, following first-line therapy, during clinical treatment, or any combination thereof.

For example, a biological sample taken from a patient may be analyzed to determine whether a condition or disease, such as cancer, that the patient is or may be suffering from is one which is characterized by a genetic abnormality or abnormal protein expression which leads to up-regulation of the levels or activity of FGFR or to sensitization of a pathway to normal FGFR activity, or to upregulation of these growth factor signaling pathways such as growth factor ligand levels or growth factor ligand activity or to upregulation of a biochemical pathway downstream of FGFR activation.

Examples of such abnormalities that result in activation or sensitization of the FGFR signal include loss of, or inhibition of apoptotic pathways, up-regulation of the receptors or ligands, or presence of genetic alterations of the receptors or ligands e.g. PTK variants. Tumors with genetic alterations of FGFR1, FGFR2 or FGFR3 or FGFR4 or up-regulation, in particular over-expression of FGFR1, or gain-of-function genetic alterations of FGFR2 or FGFR3 may be particularly sensitive to FGFR inhibitors.

The methods, approved drug products, and uses can further comprise evaluating the presence of one or more FGFR genetic alterations in the biological sample before the administering step.

The diagnostic tests and screens are typically conducted on a biological sample selected from tumor biopsy samples, blood samples (isolation and enrichment of shed tumor cells), stool biopsies, sputum, chromosome analysis, pleural fluid, peritoneal fluid, buccal spears, biopsy, circulating DNA, or urine. In certain embodiments, the biological sample is blood, lymph fluid, bone marrow, a solid tumor sample, or any combination thereof. In certain embodiments, the biological sample is a solid tumor sample. In certain embodiments, the biological sample is a blood sample. In certain embodiments, the biological sample is a urine sample.

Methods of identification and analysis of genetic alterations and up-regulation of proteins are known to a person skilled in the art. Screening methods could include, but are not limited to, standard methods such as reverse-transcriptase polymerase chain reaction (RT PCR) or in-situ hybridization such as fluorescence in situ hybridization (FISH).

Identification of an individual carrying a genetic alteration in FGFR, in particular an FGFR genetic alteration as described herein, may mean that the patient would be particularly suitable for treatment with erdafitinib. Tumors may preferentially be screened for presence of a FGFR variant prior to treatment. The screening process will typically involve direct sequencing, oligonucleotide microarray analysis, or a mutant specific antibody. In addition, diagnosis of tumor with such genetic alteration could be performed using techniques known to a person skilled in the art and as described herein such as RT-PCR and FISH.

In addition, genetic alterations of, for example FGFR, can be identified by direct sequencing of, for example, tumor biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumor is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3rd Ed, Molecular Cloning: A Laboratory Manual, Cold Spring Harbor Laboratory Press. Alternatively, a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridization technique for assessing mRNA expression would be fluorescence in-situ hybridization (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer (SEQ ID NO: 38: ttttttttt ttttttttt tttt) for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, CA, USA), and then hybridized overnight on Human Genome Arrays.

Alternatively, the protein products expressed from the mRNAs may be assayed by immunohistochemistry of tumor samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site-specific antibodies. The skilled person will recognize that all such well-known techniques for detection of upregulation of FGFR or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumor tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8). Assay methods also include the use of markers.

Therefore, all of these techniques could also be used to identify tumors particularly suitable for treatment with the compounds of the invention.

Erdafitinib is in particular useful in treatment of a patient having a genetic altered FGFR, in particular a mutated FGFR. In certain embodiments, the HR-NMIBC or IR-NMIBC is susceptible to an FGFR2 genetic alteration and/or an FGFR3 genetic alteration. In certain embodiments, the FGFR2 or FGFR3 genetic alteration is an FGFR3 gene mutation or an FGFR2 or FGFR3 gene fusion. In some embodiments, the FGFR3 gene mutation is R248C, S249C, G370C, Y373C, or any combination thereof. In further embodiments, the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.

In certain embodiments, FGFR2 and/or FGFR3 genetic alterations can be identified using commercially available kits including, but not limiting to, a QIAGEN Therascreen® FGFR RGQ RT-PCR kit.

Pharmaceutical Compositions and Routes of Administration

In view of its useful pharmacological properties, the FGFR inhibitor generally, and erdafitinib more specifically, may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions, an effective amount of the FGFR inhibitor generally, and erdafitinib more specifically, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intra-vaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

The pharmaceutical compositions of the invention, in particular capsules and/or tablets, may include one or more pharmaceutically acceptable excipients (pharmaceutically acceptable carrier) such as disintegrants, diluents, fillers, binders, buffering agents, lubricants, glidants, thickening agents, sweetening agents, flavors, colorants, preservatives and the like. Some excipients can serve multiple purposes.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 2.5 to about 15% w/w and preferably range from about 2.5 to 7% w/w, in particular range from about 2.5 to 5% w/w. Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™). Preferred are microcrystalline cellulose and mannitol. The total amount of diluent or filler in the pharmaceutical compositions of the present invention may conveniently range from about 20% to about 95% w/w and preferably ranges from about 55% to about 95% w/w, or from about 70% to about 95% w/w, or from about 80% to about 95% w/w, or from about 85% to about 95%.

Lubricants and glidants can be employed in the manufacture of certain dosage forms and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal silica, magnesium stearate being preferred. A preferred glidant is colloidal anhydrous silica.

If present, glidants generally comprise 0.2 to 7.0% w/w of the total composition weight, in particular 0.5 to 1.5% w/w, more in particular 1 to 1.5% w/w.

If present, lubricants generally comprise 0.2 to 7.0% w/w of the total composition weight, in particular 0.2 to 2% w/w, or 0.5 to 2% w/w, or 0.5 to 1.75% w/w, or 0.5 to 1.5% w/w.

Binders can optionally be employed in the pharmaceutical compositions of the present invention. Suitable binders are water-soluble polymers, such as alkylcelluloses such as methylcellulose; hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectines such as sodium carboxymethylamylopectine; chitin derivates such as chitosan; di-, oligo- and polysaccharides such as trehalose, cyclodextrins and derivatives thereof, alginic acid, alkali metal and ammonium salts thereof, carrageenans, galactomannans, tragacanth, agar agar, gummi arabicum, guar gummi and xanthan gummi; polyacrylic acids and the salts thereof; polymethacrylic acids, the salts and esters thereof, methacrylate copolymers; polyvinylpyrrolidone (PVP), polyvinylalcohol (PVA) and copolymers thereof, e.g. PVP-VA. Preferably, the water-soluble polymer is a hydroxyalkyl alkylcelluloses, such as for example hydroxypropylmethyl cellulose, e.g. hydroxypropylmethyl cellulose 15 cps.

Other excipients such as coloring agents and pigments may also be added to the compositions of the invention. Coloring agents and pigments include titanium dioxide and dyes suitable for food. A coloring agent or a pigment is an optional ingredient in the formulation of the invention, but when used the coloring agent can be present in an amount up to 3.5% w/w based on the total composition weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

Formaldehyde scavengers are compounds that are capable of absorbing formaldehyde. They include compounds comprising a nitrogen center that is reactive with formaldehyde, such as to form one or more reversible or irreversible bonds between the formaldehyde scavenger and formaldehyde. For example, the formaldehyde scavenger comprises one or more nitrogen atoms/centers that are reactive with formaldehyde to form a schiff base imine that is capable of subsequently binding with formaldehyde. For example, the formaldehyde scavenger comprises one or more nitrogen centers that are reactive with formaldehyde to form one or more 5-8 membered cyclic rings. The formaldehyde scavenger preferably comprises one or more amine or amide groups. For example, the formaldehyde scavenger can be an amino acid, an amino sugar, an alpha amine compound, or a conjugate or derivative thereof, or a mixture thereof. The formaldehyde scavenger may comprise two or more amines and/or amides.

Formaldehyde scavengers include, for example, glycine, alanine, serine, threonine, cysteine, valine, lecuine, isoleucine, methionine, phenylalanine, tyrosine, aspartic acid, glutamic acid, arginine, lysine, ornithine, citrulline, taurine pyrrolysine, meglumine, histidine, aspartame, proline, tryptophan, citrulline, pyrrolysine, asparagine, glutamine, or a conjugate or mixture thereof; or, whenever possible, pharmaceutically acceptable salts thereof.

In an aspect of the invention, the formaldehyde scavenger is meglumine or a pharmaceutically acceptable salt thereof, in particular meglumine base.

In an embodiment, in the methods and uses as described herein, erdafitinib is administered or is to be administered as a pharmaceutical composition, in particular a tablet or capsule, comprising erdafitinib or a pharmaceutically acceptable salt thereof, in particular erdafitinib base; a formaldehyde scavenger, in particular meglumine or a pharmaceutically acceptable salt thereof, in particular meglumine base; and a pharmaceutically acceptable carrier.

It is another object of the invention to provide a process of preparing a pharmaceutical composition as described herein, in particular in the form of a tablet or a capsule, characterized by blending a formaldehyde scavenger, in particular meglumine, and erdafitinib, a pharmaceutically acceptable salt thereof or a solvate thereof, in particular erdafitinib base, with a pharmaceutically acceptable carrier and compressing said blend into tablets or filling said blend in capsules.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. Preferred forms are tablets and capsules.

In certain embodiments, the FGFR inhibitor is present in a solid unit dosage form, and a solid unit dosage form suitable for oral administration. The unit dosage form may contain about 1, 2, 3, 4, 5, 6, 7, 8, 9, or 10 mg of the FGFR inhibitor per unit dose form or an amount in a range bounded by two of these values, in particular 3, 4 or 5 mg per unit dose.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

Tablets or capsules of the present invention may further be film-coated e.g. to improve taste, to provide ease of swallowing and an elegant appearance. Polymeric film-coating materials are known in the art. Preferred film coatings are water-based film coatings opposed to solvent based film coatings because the latter may contain more traces of aldehydes. A preferred film-coating material is Opadry® II aqueous film coating system, e.g. Opadry® II 85F, such as Opadry® II 85F92209. Further preferred film coatings are water-based film coatings that protects from environmental moisture, such as Readilycoat® (e.g. Readilycoat® D), AquaPolish® MS, Opadry® amb, Opadry® amb II, which are aqueous moisture barrier film coating systems. A preferred film-coating is Opadry® amb II, a high performance moisture barrier film coating which is a PVA-based immediate release system, without polyethylene glycol.

In tablets according to the invention, the film coat in terms of weight preferably accounts for about 4% (w/w) or less of the total tablet weight.

For capsules according to the present invention, hypromellose (HPMC) capsules are preferred over gelatin capsules.

In an aspect of the invention, the pharmaceutical compositions as described herein, in particular in the form of a capsule or a tablet, comprise from 0.5 mg to 20 mg base equivalent, or from 2 mg to 20 mg base equivalent, or from 0.5 mg to 12 mg base equivalent, or from 2 mg to 12 mg base equivalent, or from 2 mg to 10 mg base equivalent, or from 2 mg to 6 mg base equivalent, or 2 mg base equivalent, 3 mg base equivalent, 4 mg base equivalent, 5 mg base equivalent, 6 mg base equivalent, 7 mg base equivalent, 8 mg base equivalent, 9 mg base equivalent, 10 mg base equivalent, 11 mg base equivalent or 12 mg base equivalent of erdafitinib, a pharmaceutically acceptable salt thereof or a solvate thereof. In particular, the pharmaceutical compositions as described herein comprise 3 mg base equivalent, 4 mg base equivalent or 5 mg base equivalent of erdafitinib, a pharmaceutically acceptable salt thereof or a solvate thereof, in particular 3 mg or 4 mg or 5 mg of erdafitinib base.

In an aspect of the invention, the pharmaceutical compositions as described herein, in particular in the form of a capsule or a tablet, comprise from 0.5 mg to 20 mg, or from 2 mg to 20 mg, or from 0.5 mg to 12 mg, or from 2 mg to 12 mg, or from 2 mg to 10 mg, or from 2 mg to 6 mg, or 2 mg, 3 mg, 4 mg, 5 mg, 6 mg, 7 mg, 8 mg, 9 mg, 10 mg, 11 mg or 12 mg of erdafitinib base. In particular, the pharmaceutical compositions as described herein comprise 3 mg, 4 mg or 5 mg of erdafitinib base. In particular, the pharmaceutical compositions as described herein comprise 3 mg, 4 mg or 5 mg of erdafitinib base and from about 0.5 to about 5% w/w, from about 0.5 to about 3% w/w, from about 0.5 to about 2% w/w, from about 0.5 to about 1.5% w/w, or from about 0.5 to about 1% w/w of a formaldehyde scavenger, in particular meglumine. In particular, the pharmaceutical compositions as described herein comprise 3 mg, 4 mg or 5 mg of erdafitinib base and from about 0.5 to about 1.5% w/w or from about 0.5 to about 1% w/w of a formaldehyde scavenger, in particular meglumine.

In an aspect of the invention, more than one, e.g. two, pharmaceutical compositions as described herein can be administered in order to obtain a desired dose, e.g. a daily dose. For example, for a daily dose of 8 mg base equivalent of erdafitinib, 2 tablets or capsules of 4 mg erdafitinib base equivalent each may be administered; or a tablet or a capsule of 3 mg erdafitinib base equivalent and a tablet or capsule of 5 mg base equivalent may be administered. For example, for a daily dose of 9 mg base equivalent of erdafitinib, 3 tablets or capsules of 3 mg erdafitinib base equivalent each may be administered; or a tablet or a capsule of 4 mg erdafitinib base equivalent and a tablet or capsule of 5 mg base equivalent may be administered. For example, for a daily dose of 6 mg base equivalent of erdafitinib, 2 tablets or capsules of 3 mg erdafitinib base equivalent each may be administered.

The amount of formaldehyde scavenger, in particular meglumine, in the pharmaceutical compositions according to the present invention may range from about 0.1 to about 10% w/w, about 0.1 to about 5% w/w, from about 0.1 to about 3% w/w, from about 0.1 to about 2% w/w, from about 0.1 to about 1.5% w/w, from about 0.1 to about 1% w/w, from about 0.5 to about 5% w/w, from about 0.5 to about 3% w/w, from about 0.5 to about 2% w/w, from about 0.5 to about 1.5% w/w, from about 0.5 to about 1% w/w.

According to particular embodiments, erdafitinib is supplied as 3 mg, 4 mg or 5 mg film-coated tablets for oral administration and contains the following inactive ingredients or equivalents thereof: Tablet Core: croscarmellose sodium, magnesium stearate, mannitol, meglumine, and microcrystalline cellulose; and Film Coating: Opadry amb II: Glycerol monocaprylocaprate Type I, polyvinyl alcohol-partially hydrolyzed, sodium lauryl sulfate, talc, titanium dioxide, iron oxide yellow, iron oxide red (for orange and brown tablets), ferrosoferric oxide/iron oxide black (for brown tablets).

Studies that look at safety seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

The term "acceptable" with respect to a formulation, composition or ingredient, as used herein, means that the beneficial effects of that formulation, composition or ingredient on the general health of the human being treated substantially outweigh its detrimental effects, to the extent any exist.

All formulations for oral administration are in dosage form suitable for such administration.

Methods of Dosing and Treatment Regimens

In one aspect, described herein are methods of treating HR-NMIBC or IR-NMIBC comprising, consisting of, or consisting essentially of administering a therapeutically effective amount of an FGFR inhibitor to a patient that has been diagnosed with HR-NMIBC or IR-NMIBC, wherein the FGFR inhibitor is administered orally. In some embodiments, the FGFR inhibitor generally, and erdafitinib specifically is administered daily, in particular once daily. In some embodiments, the FGFR inhibitor generally, and erdafitinib specifically is administered twice-a-day. In some embodiments, the FGFR inhibitor generally, and erdafitinib specifically is administered three times a day. In some embodiments, the FGFR inhibitor generally, and erdafitinib specifically is administered four times a day. In some embodiments, the FGFR inhibitor generally, and erdafitinib specifically is administered every other day. In some embodiments, the FGFR inhibitor generally, and erdafitinib specifically is administered weekly. In some embodiments, the FGFR inhibitor generally, and erdafitinib specifically is administered twice a week. In some embodiments, the FGFR inhibitor generally, and erdafitinib specifically is administered every other week. In some embodiments, the FGFR inhibitor generally, and erdafitinib specifically is administered orally on a continuous daily dosage schedule.

In general, doses of the FGFR inhibitor, and erdafitinib specifically, employed for treatment of the diseases or conditions described herein in humans are typically in the range of about 1 to 20 mg per day. In some embodiments, the FGFR inhibitor, and erdafitinib specifically, is administered orally to the human at a dose of about 1 mg per day, about 2 mg per day, about 3 mg per day, about 4 mg per day, about 5 mg per day, about 6 mg per day, about 7 mg per day, about 8 mg per day, about 9 mg per day, about 10 mg per day, about 11 mg per day, about 12 mg per day, about 13 mg per day, about 14 mg per day, about 15 mg per day, about 16 mg per day, about 17 mg per day, about 18 mg per day, about 19 mg per day or about 20 mg per day.

In some embodiments, erdafitinib is administered orally. In certain embodiments, erdafitinib is administered orally at a dose of about 8 mg once daily. In further embodiments, the dose of erdafitinib is increased from 8 mg once daily to 9 mg once daily. In still further embodiments, the dose of erdafitinib is increased from 8 mg once daily to 9 mg once daily at 14 to 21 days after initiating treatment if. (a) the patient exhibits a serum phosphate ($PO_4$) level that is less than about 5.5 mg/dL at 14-21 days after initiating treatment and administration of erdafitinib at 8 mg once daily resulted in no ocular disorder; or (b) administration of erdafitinib at 8 mg once daily resulted in no Grade 2 or greater adverse reaction. In certain embodiments, the dose of erdafitinib is increased from 8 mg once daily to 9 mg once daily at 14 days after initiating treatment. In certain embodiments, the dose of erdafitinib is increased from 8 mg once daily to 9 mg once daily at 15 days after initiating treatment. In certain embodiments, the dose of erdafitinib is increased from 8 mg once daily to 9 mg once daily at 16 days after initiating treatment. In certain embodiments, the dose of erdafitinib is increased from 8 mg once daily to 9 mg once daily at 17 days after initiating treatment. In certain embodiments, the dose of erdafitinib is increased from 8 mg once daily to 9 mg once daily at 18 days after initiating treatment. In certain embodiments, the dose of erdafitinib is increased from 8 mg once daily to 9 mg once daily at 19 days after initiating treatment. In certain embodiments, the dose of erdafitinib is increased from 8 mg once daily to 9 mg once daily at 20 days after initiating treatment. In certain embodiments, the dose of erdafitinib is increased from 8 mg once daily to 9 mg once daily at 21 days after initiating treatment.

In an embodiment, erdafitinib is administered at a dose of 8 mg, in particular 8 mg once daily. In an embodiment, erdafitinib is administered at a dose of 8 mg, in particular 8 mg once daily, with an option to uptitrate to 9 mg depending on serum phosphate levels (e.g. serum phosphate levels are <5.5 mg/dL, or are <7 mg/dL or range from and include 7 mg/dL to ≤9 mg/dL or are ≤9 mg/dL), and depending on treatment-related adverse events observed. In an embodiment, the levels of serum phosphate for determining whether or not to up-titrate are measured on a treatment day during the first cycle of erdafitinib treatment, in particular on day 14±2 days, more in particular on day 14, of erdafitinib administration.

In an embodiment, erdafitinib is administered at a dose of 6 mg, in particular 6 mg once daily, in particular on a continuous schedule.

In an embodiment, erdafitinib is administered at a dose of 6 mg, in particular 6 mg once daily. In an embodiment, erdafitinib is administered at a dose of 6 mg, in particular 6 mg once daily, with an option to uptitrate to 8 mg depending on serum phosphate levels (e.g. serum phosphate levels are <5.5 mg/dL), and depending on treatment-related adverse events observed. In an embodiment, the levels of serum phosphate for determining whether or not to up-titrate are measured on a treatment day at the end of cycle 1 treatment period, in particular at day 1 of cycle 2 (C2D1)±7 days or at day 1 of cycle 2 (C2D1)±3 days, more in particular at C2D1, of erdafitinib administration.

In certain embodiments, the dose of erdafitinib is increased from 6 mg once daily to 8 mg once daily at the end of cycle 1 treatment period, in particular at day 1 of cycle 2 (C2D1)±7 days or at day 1 of cycle 2 (C2D1)±3 days, more in particular at C2D1.

In some embodiments, erdafitinib is administered orally. In certain embodiments, erdafitinib is administered orally at a dose of about 6 mg once daily. In further embodiments, the dose of erdafitinib is increased from 6 mg once daily to 8 mg once daily. In still further embodiments, the dose of erdafitinib is increased from 6 mg once daily to 8 mg once daily at the end of cycle 1 treatment period, in particular at day 1 of cycle 2 (C2D1)±7 days or at day 1 of cycle 2 (C2D1)±3 days, more in particular at C2D1, after initiating treatment if: (a) the patient exhibits a serum phosphate ($PO_4$) level that is less than about 5.5 mg/dL at the end of cycle 1 treatment period, in particular at day 1 of cycle 2 (C2D1)±7 days or at day 1 of cycle 2 (C2D1)±3 days, more in particular at C2D1, after initiating treatment and administration of erdafitinib at 6 mg once daily resulted in no significant toxicity, e.g. no ocular disorder; or (b) administration of erdafitinib at 6 mg once daily resulted in no Grade 2 or greater adverse reaction.

In some embodiments, erdafitinib is administered orally. In certain embodiments, erdafitinib is administered orally at a dose of about 6 mg once daily. In further embodiments, erdafitinib remains to be administered orally at a dose of about 6 mg once daily at the end of cycle 1 treatment period, in particular at day 1 of cycle 2 (C2D1)±7 days or at day 1 of cycle 2 (C2D1)±3 days, more in particular at C2D1, after initiating treatment if. (a) the patient exhibits a serum phosphate ($PO_4$) level of 5.5 mg/dL to 6.99 mg/dL at the end of cycle 1 treatment period, in particular at day 1 of cycle 2 (C2D1)±7 days or at day 1 of cycle 2 (C2D1)±3 days, more in particular at C2D1, after initiating treatment and administration of erdafitinib at 6 mg once daily resulted in no significant toxicity, e.g. no ocular disorder; or (b) administration of erdafitinib at 6 mg once daily resulted in no Grade 2 or greater adverse reaction. In an embodiment, phosphate intake is restricted to 600-800 mg/day.

In some embodiments, erdafitinib is administered orally. In certain embodiments, erdafitinib is administered orally at a dose of about 6 mg once daily. In further embodiments, erdafitinib remains to be administered orally at a dose of about 6 mg once daily at the end of cycle 1 treatment period, in particular at day 1 of cycle 2 (C2D1)±7 days or at day 1 of cycle 2 (C2D1)±3 days, more in particular at C2D1, after initiating treatment if: (a) the patient exhibits a serum phosphate ($PO_4$) level≥7 mg/dL at the end of cycle 1 treatment period, in particular at day 1 of cycle 2 (C2D1)±7 days or at day 1 of cycle 2 (C2D1)±3 days, more in particular at C2D1, after initiating treatment, or (b) the presence of other toxicity; and the serum phosphate ($PO_4$) toxicity management of Table 7 is applied.

TABLE 7

Guidelines for Management of Serum Phosphate Elevation

| Serum Phosphate Level | Study Drug Management | Symptom Management |
|---|---|---|
| <5.50 mg/dL (<1.75 mmol/L) (Grade 0) | Continue erdafitinib treatment. | None. |
| 5.50-6.99 mg/dL (1.75-2.24 mmol/L) (Grade 1) | Continue erdafitinib treatment. | Restriction of phosphate intake to 600-800 mg/day. |
| 7.00-8.99 mg/dL (2.25-2.90 mmol/L) (Grade 2) | Continue erdafitinib treatment. A dose reduction will be implemented for persistent[a] hyperphosphatemia (defined as serum phosphate ≥7 mg/dL for a period of 2 months) or if clinically necessary (eg, in the presence of additional adverse events linked to hyperphosphatemia or electrolyte disturbances) | Restriction of phosphate intake to 600-800 mg/day. Start sevelamer 800 to 1,600 mg TID with food until phosphate level is <7.0 mg/dL. |
| 9.00-10.00 mg/dL (>2.91-3.20 mmol/L) (Grade 3) | Withhold[b] erdafitinib treatment until serum phosphate level returns to <7.0 mg/dL (weekly testing recommended). Restart treatment at the same dose level. A dose reduction will be implemented for persistent[a] hyperphosphatemia (defined as serum phosphate ≥9 mg/dL for a period of 1 month) or if clinically necessary (eg, in the presence of additional adverse events linked to hyperphosphatemia or electrolyte disturbances) | Restriction of phosphate intake to 600-800 mg/day. Sevelamer up to 1,600 mg TID with food until serum phosphate level is <7.0 mg/dL. |
| >10.00 mg/dL (>3.20 mmol/L) (Grade 4) | Withhold[b] erdafitinib treatment until serum phosphate level returns to <7.0 mg/dL (weekly testing recommended). Restart treatment at the first reduced dose level. If persistent[a] hyperphosphatemia (≥10.00 mg/dL) for >2 weeks, erdafitinib must be discontinued permanently. | Medical management as clinically appropriate. |
| Significant alteration in baseline renal function or Grade 3 hypocalcemia | Erdafitinib must be discontinued permanently. (In situations where the subject is having clinical benefit and the investigator and the sponsor's medical monitor agree that continuation of treatment is in the best interest of the subject, the drug may be restarted at 2 dose levels lower if appropriate. Follow other recommendations described above, Section Error! Reference source not found. ) | Medical management as clinically appropriate. |

Note:

These are general guidelines. The treating physicians must use clinical judgment and local standard of care to decide the best way to manage phosphate elevation. If sevelamer hydrochloride (Renagel ®) is not available, use of other phosphate binders (non-calcium containing) based on the local standard is recommended, including sevelamer carbonate (Renvela) or lanthanum carbonate (Fosrenol ®). Additional information on phosphorous in foods by class of food can also be found at ww.permanente.net/homepage/kaiser/pdf/42025.pdf. Additional information for phosphate management and diet can be found at the National Kidney Foundation website (http://www.kidney.org/atoz/content/phosphoms.cfm)

[a]Persistent hyperphosphatemia is considered to be more than 1 sequential phosphate value above the cut-off.

[b]Study drug interruptions for hyperphosphatemia suggested to be 7 days in duration.

TID = 3 times a day

Table 7 reports guidelines for the clinical management of elevated serum phosphate levels during erdafitinib treatment.

Table 8 reports the 6 mg daily dose schedule (with up-titration) and dose reductions.

TABLE 8

Dose Schedule and Dose Reductions - 6 mg Daily Dosing (with Up-titration)

| Category | With Up-titration |
|---|---|
| Starting dose | 6 mg |
| Up-titration | 8 mg |
| 1st dose reduction | 6 mg |
| 2nd dose reduction | 5 mg |

TABLE 8-continued

| Dose Schedule and Dose Reductions - 6 mg Daily Dosing (with Up-titration) | |
|---|---|
| Category | With Up-titration |
| 3rd dose reduction | 4 mg |
| 4th dose reduction | STOP |

In an embodiment, the treatment cycle as used herein is a 28-day cycle. In certain embodiments, the treatment cycle is a 28-day cycle for up to two years.

In one embodiment, the desired dose is conveniently presented in a single dose or in divided doses administered simultaneously (or over a short period of time) or at appropriate intervals, for example as two, three, four or more sub-doses per day. In some embodiments, the FGFR inhibitor is conveniently presented in divided doses that are administered simultaneously (or over a short period of time) once a day. In some embodiments, the FGFR inhibitor generally, and erdafitinib specifically, is conveniently presented in divided doses that are administered in equal portions twice-a-day. In some embodiments, the FGFR inhibitor generally, and erdafitinib specifically, is conveniently presented in divided doses that are administered in equal portions three times a day. In some embodiments, the FGFR inhibitor is conveniently presented in divided doses that are administered in equal portions four times a day.

In certain embodiments, the desired dose may be delivered in 1, 2, 3, 4, 5, 6, 7, 8, 9, or 10 fractional unit dosages throughout the course of the day, such that the total amount of FGFR inhibitor generally, and erdafitinib specifically, delivered by the fractional unit dosages over the course of the day provides the total daily dosages.

In some embodiments, the amount of the FGFR inhibitor generally, and erdafitinib specifically, that is given to the human varies depending upon factors such as, but not limited to, condition and severity of the disease or condition, and the identity (e.g., weight) of the human, and the particular additional therapeutic agents that are administered (if applicable).

In still further embodiments, erdafitinib is not co-administered with strong CYP3A4 inhibitors or inducers or moderate CyP3A4 inducers. In certain embodiments, erdafitinib is not co-administered with strong CYP3A4 inhibitors or inducers or moderate CyP3A4 inducers within 14 days or 5 half-lives before the first dose of study drug.

Non-limiting examples of strong CYP3A4 inhibitors include Boceprevir, Aprepitant, Clarithromycin, Conivaptan, grapefruit juice, Indinavir, Lopinavir Itraconazole, Mibefradil Ketoconazole, Nefazodone, Ritonavir, Posaconazole, Nelfinavir, Saquinavir, Conivaptan, Telaprevir, Boceprevir, Telithromycin, Clarithromycin, Voriconazole, Clotrimazole, Diltiazem, Erythromycin, Fluconazole, Verapamil, and Troleandomycin.

Non-limiting examples of moderate to strong CYP3A4 inducers include Avasimibe, St. John's wort, Carbamazepine, Efavirenz, Phenytoin, Etravirine, Bosentan, Nafcillin, Rifampin, Modafinil, Rifabutin, and Barbiturates.

Kits/Articles of Manufacture

For use in the method or uses described herein, kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Nucleotide Sequences of FGFR Fusion Genes

The nucleotide sequences for the FGFR fusion cDNA are provided in Table 4. The underlined sequences correspond to either FGFR3 or FGFR2, the sequences in black represent the fusion partners.

TABLE 4

| | |
|---|---|
| FGFR3-TACC3 V1<br>(2850 base pairs)<br>(SEQ ID NO: 33) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA |

TABLE 4-continued

| | |
|---|---|
| | GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCGGCTGTGACGCTCTGCCGC<br>CTGCGCAGCCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC<br>AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT<br>GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTAAAG<br>GCGACACAGGAGGAGAACCGGGAGCTGAGGAGCAGGTGTGAGGAGCTCCACGG<br>GAAGAACCTGGAACTGGGGAAGATCATGGACAGGTTCGAAGAGGTTGTGTACCA<br>GGCCATGGAGGAAGTTCAGAAGCAGAAGGAACTTTCCAAAGCTGAAATCCAGAA<br>AGTTCTAAAAGAAAAAGACCAACTTACCACAGATCTGAACTCCATGGAGAAGTC<br>CTTCTCCGACCTCTTCAAGCGTTTTGAGAAACAGAAAGAGGTGATCGAGGGCTAC<br>CGCAAGAACGAAGAGTCACTGAAGAAGTGCGTGGAGGATTACCTGGCAAGGATC<br>ACCCAGGAGGGCCAGAGGTACCAAGCCCTGAAGGCCCACGCGGAGGAGAAGCT<br>GCAGCTGGCAAACGAGGAGATCGCCCAGGTCCGGAGCAAGGCCCAGGCGGAAG<br>CGTTGGCCCTCCAGGCCAGCCTGAGGAAGGAGCAGATGCGCATCCAGTCGCTGG<br>AGAAGACAGTGGAGCAGAAGACTAAAGAGAACGAGGAGCTGACCAGGATCTGC<br>GACGACCTCATCTCCAAGATGGAGAAGATCTGA |
| FGFR3-TACC3 V3<br>(2955 base pairs)<br>(SEQ ID NO: 34 | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCGGCTGTGACGCTCTGCCGC<br>CTGCGCAGCCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC |

TABLE 4-continued

| | |
|---|---|
| | AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT<br>GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTGCCAG<br>GCCCACCCCCAGGTGTTCCCGCGCCTGGGGGCCCACCCCTGTCCACCGGACCTAT<br>AGTGGACCTGCTCCAGTACAGCCAGAAGGACCTGGATGCAGTGGTAAAGGCGAC<br>ACAGGAGGAGAACCGGGAGCTGAGGAGCAGGTGTGAGGAGCTCCACGGGAAGA<br>ACCTGGAACTGGGGAAGATCATGGACAGGTTCGAAGAGGTTGTGTACCAGGCCA<br>TGGAGGAAGTTCAGAAGCAGAAGGAACTTTCCAAAGCTGAAATCCAGAAAGTTC<br>TAAAAGAAAAAGACCAACTTACCACAGATCTGAACTCCATGGAGAAGTCCTTCT<br>CCGACCTCTTCAAGCGTTTTGAGAAACAGAAAGAGGTGATCGAGGGCTACCGCA<br>AGAACGAAGAGTCACTGAAGAAGTGCGTGGAGGATTACCTGGCAAGGATCACCC<br>AGGAGGGCCAGAGGTACCAAGCCCTGAAGGCCCACGCGGAGGAGAAGCTGCAG<br>CTGGCAAACGAGGAGATCGCCCAGGTCCGGAGCAAGGCCCAGGCGGAAGCGTTG<br>GCCCTCCAGGCCAGCCTGAGGAAGGAGCAGATGCGCATCCAGTCGCTGGAGAAG<br>ACAGTGGAGCAGAAGACTAAAGAGAACGAGGAGCTGACCAGGATCTGCGACGA<br>CCTCATCTCCAAGATGGAGAAGATCTGA |
| FGFR3-BAIAP2L1<br>(3765 base pairs)<br>(SEQ ID NO: 35) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGTCCTGGATCAGTGAGAGTGTGGAGGCCGACGTGCGCCTCCGCCT<br>GGCCAATGTGTCGGAGCGGGACGGGGGCGAGTACCTCTGTCGAGCCACCAATTT<br>CATAGGCGTGGCCGAGAAGGCCTTTTGGCTGAGCGTTCACGGGCCCCGAGCAGC<br>CGAGGAGGAGCTGGTGGAGGCTGACGAGGCGGGCAGTGTGTATGCAGGCATCCT<br>CAGCTACGGGGTGGGCTTCTTCCTGTTCATCCTGGTGGTGGCGGCTGTGACGCTC<br>TGCCGCCTGCGCAGCCCCCCCAAGAAAGGCCTGGGCTCCCCCACCGTGCACAAG<br>ATCTCCCGCTTCCCGCTCAAGCGACAGGTGTCCCTGGAGTCCAACGCGTCCATGA<br>GCTCCAACACACCACTGGTGCGCATCGCAAGGCTGTCCTCAGGGGAGGGCCCCA<br>CGCTGGCCAATGTCTCCGAGCTCGAGCTGCCTGCCGACCCCAAATGGGAGCTGTC<br>TCGGGCCCGGCTGACCCTGGGCAAGCCCCTTGGGGAGGGCTGCTTCGGCCAGGT<br>GGTCATGGCGGAGGCCATCGGCATTGACAAGGACCGGGCCGCCAAGCCTGTCAC<br>CGTAGCCGTGAAGATGCTGAAAGACGATGCCACTGACAAGGACCTGTCGGACCT<br>GGTGTCTGAGATGGAGATGATGAAGATGATCGGGAAACACAAAAACATCATCAA<br>CCTGCTGGGCGCCTGCACGCAGGGCGGGCCCCTGTACGTGCTGGTGGAGTACGC<br>GGCCAAGGGTAACCTGCGGGAGTTTCTGCGGGCGCGGCGGCCCCCGGGCCTGGA<br>CTACTCCTTCGACACCTGCAAGCCGCCCGAGGAGCAGCTCACCTTCAAGGACCTG<br>GTGTCCTGTGCCTACCAGGTGGCCCGGGGCATGGAGTACTTGGCCTCCCAGAAGT<br>GCATCCACAGGGACCTGGCTGCCCGCAATGTGCTGGTGACCGAGGACAACGTGA<br>TGAAGATCGCAGACTTCGGGCTGGCCCGGGACGTGCACAACCTCGACTACTACA<br>AGAAGACGACCAACGGCCGGCTGCCCGTGAAGTGGATGGCGCCTGAGGCCTTGT<br>TTGACCGAGTCTACACTCACCAGAGTGACGTCTGGTCCTTTGGGGTCCTGCTCTG<br>GGAGATCTTCACGCTGGGGGGCTCCCCGTACCCCGGCATCCCTGTGGAGGAGCTC<br>TTCAAGCTGCTGAAGGAGGGCCACCGCATGGACAAGCCCGCCAACTGCACACAC<br>GACCTGTACATGATCATGCGGGAGTGCTGGCATGCCGCGCCCTCCCAGAGGCCC<br>ACCTTCAAGCAGCTGGTGGAGGACCTGGACCGTGTCCTTACCGTGACGTCCACCG<br>ACAATGTTATGGAACAGTTCAATCCTGGGCTGCGAAATTTAATAAACCTGGGGA<br>AAAATTATGAGAAAGCTGTAAACGCTATGATCCTGGCAGGAAAAGCCTACTACG<br>ATGGAGTGGCCAAGATCGGTGAGATTGCCACTGGGTCCCCCGTGTCAACTGAACT<br>GGGACATGTCCTCATAGAGATTTCAAGTACCCACAAGAAACTCAACGAGAGTCT<br>TGATGAAAATTTTAAAAAATTCCACAAAGAGATTATCCATGAGCTGGAGAAGAA<br>GATAGAACTTGACGTGAAATATATGAACGCAACTCTAAAAAGATACCAAACAGA<br>ACACAAGAATAAATTAGAGTCTTTGGAGAAATCCCAAGCTGAGTTGAAGAAGAT<br>CAGAAGGAAAAGCCAAGGAAGCCGAAACGCACTCAAATATGAACACAAAGAAA<br>TTGAGTATGTGGAGACCGTTACTTCTCGTCAGAGTGAAATCCAGAAATTCATTGC<br>AGATGGTTGCAAAGAGGCTCTGCTTGAAGAGAAGAGGCGCTTCTGCTTTCTGGTT<br>GATAAGCACTGTGGCTTTGCAAACCACATACATTATTATCACTTACAGTCTGCAG<br>AACTACTGAATTCCAAGCTGCCTCGGTGGCAGGAGACCTGTGTTGATGCCATCAA<br>AGTGCCAGAGAAAATCATGAATATGATCGAAGAAATAAAGACCCCAGCCTCTAC<br>CCCCGTGTCTGGAACTCCTCAGGCTTCACCCATGATCGAGAGAAGCAATGTGGTT<br>AGGAAAGATTACGACACCCTTTCTAAATGCTCACCAAAGATGCCCCCCGCTCCTT<br>CAGGCAGAGCATATACCAGTCCCTTGATCGATATGTTTAATAACCCAGCCACGGC |

TABLE 4-continued

| | |
|---|---|
| | TGCCCCGAATTCACAAAGGGTAAATAATTCAACAGGTACTTCCGAAGATCCCAGT<br>TTACAGCGATCAGTTTCGGTTGCAACGGGACTGAACATGATGAAGAAGCAGAAA<br>GTGAAGACCATCTTCCCGCACACTGCGGGCTCCAACAAGACCTTACTCAGCTTTG<br>CACAGGGAGATGTCATCACGCTGCTCATCCCCGAGGAGAAGGATGGCTGGCTCT<br>ATGGAGAACACGACGTGTCCAAGGCGAGGGGTTGGTTCCCGTCGTCGTACACGA<br>AGTTGCTGGAAGAAAATGAGACAGAAGCAGTGACCGTGCCCACGCCAAGCCCCA<br>CACCAGTGAGAAGCATCAGCACCGTGAACTTGTCTGAGAATAGCAGTGTTGTCAT<br>CCCCCCACCCGACTACTTGGAATGCTTGTCCATGGGGGCAGCTGCCGACAGGAG<br>AGCAGATTCGGCCAGGACGACATCCACCTTTAAGGCCCCAGCGTCCAAGCCCGA<br>GACCGCGGCTCCTAACGATGCCAACGGGACTGCAAAGCCGCCTTTTCTCAGCGG<br>AGAAAACCCCTTTGCCACTGTGAAACTCCGCCCGACTGTGACGAATGATCGCTCG<br>GCACCCATCATTCGATGA |
| FGFR2-BICC1<br>(4989 base pairs)<br>(SEQ ID NO: 36) | >ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAAGGAGATTACAGCTTCCCCAGACTACCTGGAGATAGCCATTTACT<br>GCATAGGGGTCTTCTTAATCGCCTGTATGGTGGTAACAGTCATCCTGTGCCGAAT<br>GAAGAACACGACCAAGAAGCCAGACTTCAGCAGCCAGCCGGCTGTGCACAAGCT<br>GACCAAACGTATCCCCCTGCGGAGACAGGTAACAGTTTCGGCTGAGTCCAGCTCC<br>TCCATGAACTCCAACACCCCGCTGGTGAGGATAACAACACGCCTCTCTTCAACGG<br>CAGACACCCCCATGCTGGCAGGGGTCTCCGAGTATGAACTTCCAGAGGACCCAA<br>AATGGGAGTTTCCAAGAGATAAGCTGACACTGGGCAAGCCCCTGGGAGAAGGTT<br>GCTTTGGGCAAGTGGTCATGGCGGAAGCAGTGGGAATTGACAAAGACAAGCCCA<br>AGGAGGCGGTCACCGTGGCCGTGAAGATGTTGAAAGATGATGCCACAGAGAAAG<br>ACCTTTCTGATCTGGTGTCAGAGATGGAGATGATGAAGATGATTGGGAAACACA<br>AGAATATCATAAATCTTCTTGGAGCCTGCACACAGGATGGGCCTCTCTATGTCAT<br>AGTTGAGTATGCCTCTAAAGGCAACCTCCGAGAATACCTCCGAGCCCGGAGGCC<br>ACCCGGGATGGAGTACTCCTATGACATTAACCGTGTTCCTGAGGAGCAGATGACC<br>TTCAAGGACTTGGTGTCATGCACCTACCAGCTGGCCAGAGGCATGGAGTACTTGG<br>CTTCCCAAAAATGTATTCATCGAGATTTAGCAGCCAGAAATGTTTTGGTAACAGA<br>AAACAATGTGATGAAAATAGCAGACTTTGGACTCGCCAGAGATATCAACAATAT<br>AGACTATTACAAAAAGACCACCAATGGGCGGCTTCCAGTCAAGTGGATGGCTCC<br>AGAAGCCCTGTTTGATAGAGTATACACTCATCAGAGTGATGTCTGGTCCTTCGGG<br>GTGTTAATGTGGGAGATCTTCACTTTAGGGGGCTCGCCCTACCCAGGGATTCCCG<br>TGGAGGAACTTTTTAAGCTGCTGAAGGAAGGACACAGAATGGATAAGCCAGCCA<br>ACTGCACCAACGAACTGTACATGATGATGAGGGACTGTTGGCATGCAGTGCCCTC<br>CCAGAGACCAACGTTCAAGCAGTTGGTAGAAGACTTGGATCGAATTCTCACTCTC<br>ACAACCAATGAGATCATGGAGGAAACAAATACGCAGATTGCTTGGCCATCAAAA<br>CTGAAGATCGGAGCCAAATCCAAGAAAGATCCCCATATTAAGGTTTCTGGAAAG<br>AAAGAAGATGTTAAAGAAGCCAAGGAAATGATCATGTCTGTCTTAGACACAAAA<br>AGCAATCGAGTCACACTGAAGATGGATGTTTCACATACAGAACATTCACATGTA<br>ATCGGCAAAGGTGGCAACAATATTAAAAAAGTGATGGAAGAAACCGGATGCCAT<br>ATCCACTTTCCAGATTCCAACAGGAATAACCAAGCAGAAAAAAGCAACCAGGTA<br>TCTATAGCGGGACAACCAGCAGGAGTAGAATCTGCCCGAGTTAGAATTCGGGAG<br>CTGCTTCCTTTGGTGCTGATGTTTGAGCTACCAATTGCTGGAATTCTTCAACCGGT<br>TCCTGATCCTAATTCCCCCTCTATTCAGCATATATCACAAACGTACAATATTTCAG<br>TATCATTTAAACAGCGTTCCCGAATGTATGGTGCTACTGTCATAGTACGAGGGTC<br>TCAGAATAACACTAGTGCTGTGAAGGAAGGAACTGCCATGCTGTTAGAACATCTT<br>GCTGGGAGCTTAGCATCAGCTATTCCTGTGAGCACACAACTAGATATTGCAGCTC<br>AACATCATCTCTTTATGATGGGTCGAAATGGGAGCAACATCAAACATATCATGCA<br>GAGAACAGGTGCTCAGATCCACTTTCCTGATCCCAGTAATCCACAAAAGAAATCT<br>ACCGTCTACCTCCAGGGCACCATTGAGTCTGTCTGTCTTGCAAGGCAATATCTCA<br>TGGGTTGTCTTCCTCTTGTGTTGATGTTTGATATGAAGGAAGAAATTGAAGTAGA<br>TCCACAATTCATTGCGCAGTTGATGGAACAGCTTGATGTCTTCATCAGTATTAAA<br>CCAAAGCCCAAACAGCCAAGCAAGTCTGTGATTGTGAAAAGTGTTGAGCGAAAT<br>GCCTTAAATATGTATGAAGCAAGGAAATGTCTCCTCGGACTTGAAAGCAGTGGG<br>GTTACCATAGCAACCAGTCCATCCCCAGCATCCTGCCCTGCCGGCCTGGCATGTC<br>CCAGCCTGGATATCTTAGCTTCAGCAGGCCTTGGACTCACTGGACTAGGTCTTTT<br>GGGACCCACCACCTTATCTCTGAACACTTCAACAACCCCAAACTCACTCTTGAAT<br>GCTCTTAATAGCTCAGTCAGTCCTTTGCAAAGTCCAAGTTCTGGTACACCCAGCC<br>CCACATTATGGGCACCCCCACTTGCTAATACTTCAAGTGCCACAGGTTTTTCTGCT<br>ATACCACACCTTATGATTCCATCTACTGCCCAAGCCACATTAACTAATATTTTGTT |

TABLE 4-continued

GTCTGGAGTGCCCACCTATGGGCACACAGCTCCATCTCCCCCTCCTGGCTTGACT
CCTGTTGATGTCCATATCAACAGTATGCAGACCGAAGGCAAAAAAATCTCTGCTG
CTTTAAATGGACATGCACAGTCTCCAGATATAAAATATGGTGCAATATCCACTTC
ATCACTTGGAGAAAAAGTGCTGAGTGCAAATCACGGGGATCCGTCCATCCAGAC
AAGTGGGTCTGAGCAGACATCTCCCAAATCAAGCCCCACTGAAGGTTGTAATGA
TGCTTTTGTTGAAGTAGGCATGCCTCGAAGTCCTTCCCATTCTGGGAATGCTGGT
GACTTGAAACAGATGATGTGTCCCTCCAAGGTTTCCTGTGCCAAAAGGCAGACA
GTGGAACTATTGCAAGGCACGAAAAACTCACACTTACACAGCACTGACAGGTTG
CTCTCAGACCCTGAACTGAGTGCTACCGAAAGCCCTTTGGCTGACAAGAAGGCTC
CAGGGAGTGAGCGCGCTGCAGAGAGGGCAGCAGCTGCCCAGCAAAACTCCGAA
AGGGCCCACCTTGCTCCACGGTCATCATATGTCAACATGCAGGCATTTGACTATG
AACAGAAGAAGCTATTAGCCACCAAAGCTATGTTAAAGAAACCAGTGGTGACGG
AGGTCAGAACGCCCACAAATACCTGGAGTGGCCTGGGTTTTTCTAAATCCATGCC
AGCTGAAACTATCAAGGAGTTGAGAAGGGCCAATCATGTGTCCTATAAGCCCAC
AATGACAACCACTTATGAGGGCTCATCCATGTCCCTTTCACGGTCCAACAGTCGT
GAGCACTTGGGAGGTGGAAGCGAATCTGATAACTGGAGAGACCGAAATGGAATT
GGACCTGGAAGTCATAGTGAATTTGCAGCTTCTATTGGCAGCCCTAAGCGTAAAC
AAAACAAATCAACGGAACACTATCTCAGCAGTAGCAATTACATGGACTGCATTT
CCTCGCTGACAGGAAGCAATGGCTGTAACTTAAATAGCTCTTTCAAAGGTTCTGA
CCTCCCTGAGCTCTTCAGCAAACTGGGCCTGGGCAAATACACAGATGTTTTCCAG
CAACAAGAGATCGATCTTCAGACATTCCTCACTCTCACAGATCAGGATCTGAAGG
AGCTGGGAATAACTACTTTTGGTGCCAGGAGGAAAATGCTGCTTGCAATTTCAGA
ACTAAATAAAAACCGAAGAAAGCTTTTTGAATCGCCAAATGCACGCACCTCTTTC
CTGGAAGGTGGAGCGAGTGGAAGGCTACCCCGTCAGTATCACTCAGACATTGCT
AGTGTCAGTGGCCGCTGGTAG

FGFR2-CASP7
(3213 base pairs)
(SEQ ID NO: 37)

>ATGGTCAGCTGGGGTCGTTTCATCTGCCTGGTCGTGGTCACCATGGCAACCTTGT
CCCTGGCCCGGCCCTCCTTCAGTTTAGTTGAGGATACCACATTAGAGCCAGAAGA
GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA
ATACGGGTCCATCAATCACACGTACCACCTGGATGTTGTGGAGCGATCGCCTCAC
CGGCCCATCCTCCAAGCCGGACTGCCGGCAAATGCCTCCACAGTGGTCGGAGGA
GACGTAGAGTTTGTCTGCAAGGTTTACAGTGATGCCCAGCCCCACATCCAGTGGA
TCAAGCACGTGGAAAAGAACGGCAGTAAATACGGGCCCGACGGGCTGCCCTACC
TCAAGGTTCTCAAGGCCGCCGGTGTTAACACCACGGACAAAGAGATTGAGGTTC
TCTATATTCGGAATGTAACTTTTGAGGACGCTGGGGAATATACGTGCTTGGCGGG
TAATTCTATTGGGATATCCTTTCACTCTGCATGGTTGACAGTTCTGCCAGCGCCTG
GAAGAGAAAAGGAGATTACAGCTTCCCCAGACTACCTGGAGATAGCCATTTACT
GCATAGGGGTCTTCTTAATCGCCTGTATGGTGGTAACAGTCATCCTGTGCCGAAT
GAAGAACACGACCAAGAAGCCAGACTTCAGCAGCCAGCCGGCTGTGCACAAGCT
GACCAAACGTATCCCCCTGCGGAGACAGGTAACAGTTTCGGCTGAGTCCAGCTCC
TCCATGAACTCCAACACCCCGCTGGTGAGGATAACAACACGCCTCTCTTCAACGG
CAGACACCCCCATGCTGGCAGGGGTCTCCGAGTATGAACTTCCAGAGGACCCAA
AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGATGGCAGATGATCAGGGCTGTATTGAAGAGCAGGGGGTTGAG
GATTCAGCAAATGAAGATTCAGTGGATGCTAAGCCAGACCGGTCCTCGTTTGTAC
CGTCCCTCTTCAGTAAGAAGAAGAAAAATGTCACCATGCGATCCATCAAGACCA
CCCGGGACCGAGTGCCTACATATCAGTACAACATGAATTTTGAAAAGCTGGGCA
AATGCATCATAATAAACAACAAGAACTTTGATAAAGTGACAGGTATGGGCGTTC
GAAACGGAACAGACAAAGATGCCGAGGCGCTCTTCAAGTGCTTCCGAAGCCTGG
GTTTTGACGTGATTGTCTATAATGACTGCTCTTGTGCCAAGATGCAAGATCTGCTT
AAAAAAGCTTCTGAAGAGGACCATACAAATGCCGCCTGCTTCGCCTGCATCCTCT
TAAGCCATGGAGAAGAAAATGTAATTTATGGGAAAGATGGTGTCACACCAATAA
AGGATTTGACAGCCCACTTTAGGGGGGATAGATGCAAAACCCTTTTAGAGAAAC
CCAAACTCTTCTTCATTCAGGCTTGCCGAGGGACCGAGCTTGATGATGGCATCCA
GGCCGACTCGGGGCCCATCAATGACACAGATGCTAATCCTCGATACAAGATCCC

TABLE 4-continued

| |
|---|
| AGTGGAAGCTGACTTCCTCTTCGCCTATTCCACGGTTCCAGGCTATTACTCGTGG |
| AGGAGCCCAGGAAGAGGCTCCTGGTTTGTGCAAGCCCTCTGCTCCATCCTGGAGG |
| AGCACGGAAAAGACCTGGAAATCATGCAGATCCTCACCAGGGTGAATGACAGAG |
| TTGCCAGGCACTTTGAGTCTCAGTCTGATGACCCACACTTCCATGAGAAGAAGCA |
| GATCCCCTGTGTGGTCTCCATGCTCACCAAGGAACTCTACTTCAGTCAATAG |

Examples

These examples are provided for illustrative purposes only and not to limit the scope of the claims provided herein.

Example 1: Sensitivity of Bladder Cancer Cell Lines to Erdafitinib

Cell viability assays were performed to test the efficacy of erdafitinib in vitro. The cell lines shown in Table 5 were used in either the MTT or CellTiter-Glo assay, as described below. Both assays measure the metabolic activity of the cells but use different reagents for determination of cell viability.

MTT Assay

Cells were seeded in 96-well culture plates in 180 µl of growth medium recommended by the provider at a density that ensured continuous logarithmic growth over the 4-day incubation time. Cells were incubated 24 hours in a humidified incubator at 37° C. and 5% $CO_2$. A concentration range of erdafitinib was prepared in growth medium and 20 µl was added to the cells in each well. The cells were incubated an additional 4 days after which 25 µl of MTT (5 mg/ml in phosphate buffered saline) was added to each well. The cells were incubated for 2 hours at 37° C. and 5% $CO_2$ after which the growth medium was removed. The remaining crystals were dissolved in 125 µl glycine/DMSO buffer and optical density determined at 540 nm. Cells incubated without erdafitinib were used as untreated controls and defined as 100%. The effect of erdafitinib was determined as % of control and $IC_{50}$ values were determined from curve-fitting of the dose-response effects, as shown in Table 5.

CellTiter-Glo Assay

Cells were seeded in 96-well culture plates in 180 µl of growth medium recommended by the provider at a density that ensured continuous logarithmic growth over the 4-day incubation time. Cells were incubated 24 hours in a humidified incubator at 37° C. and 5% $CO_2$. A concentration range of erdafitinib was prepared in growth medium and 20 µl was added to the cells in each well. The cells were incubated an additional 4 days after which 100 µl of CellTiter-Glo reagent (Promega) was added to each well, the plates were shaken for 5 minutes at 500 rpm, and luminescence detected using an Envision plate reader (Perkin Elmer). Cells incubated without erdafitinib were used as untreated controls and defined as 100%. The effect of erdafitinib was determined as % of control and $IC_{50}$ values were determined from curve-fitting of the dose-response effects, as shown in Table 5.

TABLE 5

Bladder cancer cell lines - sensitivity to erdafitinib

| | Cell line | FGFR status | Tumor stage and grade | Cell viability $IC_{50}$ (nM) | Cell viability max effect (%) | Assay format |
|---|---|---|---|---|---|---|
| NMIBC | MGH-U3 | FGFR3 Y373C | Ta/T1 G1 | 2.3 | 32 | CellTiter-Glo |
| | RT4 | FGFR3-TACC3 | T1 G1/2 | 1.1 | 65 | MTT |
| | 97-7 | FGFR3 S249C | T1 G2/3 | 5 | 32 | CellTiter-Glo |
| | EJ28 | unknown | T1a G2 | 2640 | — | CellTiter-Glo |
| | T24 | WT | Ta G3 | 3330 | — | CellTiter-Glo |
| unclassified | UM-UC-1 | WT | Tx G2 | 0.96 | 80 | MTT |
| | UM-UC-14 | FGFR3 S249C | Tx G4 | 3.1 | 80 | MTT |
| | 639-V | WT/R248C? | Tx G3 | >1000 | — | CellTiter-Glo |
| | 5637 | WT | Tx G2 | 3840 | — | CellTiter-Glo |
| | CLS439 | unknown | Tx Gx | 6540 | — | CellTiter-Glo |

Conclusion

Cell viability assays demonstrated that several NMIBC cell lines (MGH-U3, RT4, and 97-7) containing FGFR3 alterations (mutations or fusion) were sensitive to low nanomolar concentrations of erdafitinib. Two cell lines for which FGFR3 was either WT (T24) or the status was unknown (EJ28) were not sensitive to erdafitinib.

Example 2: Phase 2, Multicenter, Open-Label Study (NCT04172675)

A non-limiting example of a phase 2, multicenter, open-label study to evaluate recurrence-free survival (RFS) in participants treated with erdafitinib vs investigator's choice, for participants with high-risk non-muscle-invasive bladder cancer (NMIBC) who harbor fibroblast growth factor receptor (FGFR) mutations or fusions, and who recurred after bacillus calmette-guerin (BCG) therapy.

Objective

The primary objective of this study is to evaluate RFS in patients treated with erdafitinib vs. investigator's choice of intravesical—Gemcitabine/mitomycin C (MMC)/Hyperthermic MMC therapy, for patients with HR-NMIBC who harbor FGFR mutations or fusions, and who recurred after BCG therapy.

Methods

Study Overview

Eligible patients will be screened for the presence of FGFR mutations or fusions and assigned to 1 of 3 cohorts. See FIG. 1 for a schematic of the study design.

Cohort 1 (erdafitinib and active comparator) (n=240) will include HR-NMIBC patients with papillary tumor only (carcinoma in situ (CIS) absent), with disease recurrence after BCG therapy and refuse or are not eligible for cystectomy. Patients may be BCG unresponsive or BCG experienced.

Cohort 2 (experimental) (n=20) will include HR-NMIBC, BCG unresponsive patients presenting as carcinoma in situ (CIS) with or without concurrent papillary tumor and who either refuse or are not eligible for cystectomy. This cohort is exploratory.

Cohort 3 (experimental) (n=20) will include IR-NMIBC patients presenting as papillary disease only. No predefined BCG or intravesical chemotherapy requirement. This cohort is exploratory.

Patients in Cohort 1 may be randomized in a 2:1 ratio to receive either oral erdafitinib or intravesical gemcitabine or intravesical mitomycin C (MMC)/hyperthermic MMC. Participants who are randomized to gemcitabine or MMC/hyperthermic MMC in Cohort 1 and demonstrate a recurrence via investigator disease assessment will have the opportunity to cross over to treatment with erdafitinib. Randomization will be stratified by tumor stage (Ta vs T1) and type of prior BCG therapy (BCG unresponsive vs. BCG experienced).

All patients enrolled into Cohort 2 and 3 will receive erdafitinib treatment. Erdafitinib will be discontinued in Cohort 2 if CR is not observed within 3 months. Erdafitinib will be discontinued in Cohort 3 if partial response (PR) or CR is not observed within 3 months. For Cohort 2, CR is defined as at least one of the following: 1) negative cystoscopy and negative (including atypical) urine cytology; or 2) positive cystoscopy with biopsy-proven benign or low-grade NMIBC and negative cytology. The CR rate at 6 months will be calculated with its 2-sided 95% exact CI. For Cohort 3, CR is defined as disappearance of marker lesion, with no remnant present and no viable tumor seen on histopathological examination. The CR rate will be calculated with its 2-sided 95% exact CI.

The follow-up phase will include a 30-day safety follow-up visit, disease assessment follow-up, and survival follow-up.

In cohort 1 (erdafitinib), participants may receive erdafitinib orally beginning on Cycle 1 Day 1 until 2 years of treatment have been completed, disease recurrence, intolerable toxicity, withdrawal of consent, a decision by the investigator to discontinue treatment, or study termination, whichever occurs first. Each cycle is of 28 days. The dose is 8 mg daily, and may be uptitrated to 9 mg based on phosphate level at Cycle 1 Day 14. Following a protocol amendment the dose will be changed to 6 mg daily with an option to uptitrate to 8 mg daily based on phosphate level at the end of the cycle 1 treatment period (Cycle 2 Day 1). In cohort 1 (investigator's choice), gemcitabine will be given once weekly (2,000 mg) for at least 4 doses of induction followed by monthly maintenance for at least 6 months. In cohort 1 (investigator's choice), mitomycin C will be given once weekly (40 mg dose) for at least 4 doses of induction followed by monthly maintenance for at least 6 months. In cohort 2, participants will receive erdafitinib orally beginning on Cycle 1 Day 1 until 2 years of treatment have been completed, disease recurrence, intolerable toxicity, withdrawal of consent, a decision by the investigator to discontinue treatment, or study termination, whichever occurs first. Each cycle is of 28 days. The dose is 8 mg daily, and may be uptitrated to 9 mg based on phosphate level at Cycle 1 Day 14. Following a protocol amendment the dose will be changed to 6 mg daily with an option to uptitrate to 8 mg daily based on phosphate level at the end of the cycle 1 treatment period (Cycle 2 Day 1). In cohort 3, participants will receive erdafitinib orally beginning on Cycle 1 Day 1 until 2 years of treatment have been completed, disease recurrence, intolerable toxicity, withdrawal of consent, a decision by the investigator to discontinue treatment, or study termination, whichever occurs first. Each cycle is of 28 days. The dose is 8 mg daily, and may be uptitrated to 9 mg based on phosphate level at Cycle 1 Day 14. Following a protocol amendment the dose will be changed to 6 mg daily with an option to uptitrate to 8 mg daily based on phosphate level at the end of the cycle 1 treatment period (Cycle 2 Day 1).

Inclusion and Exclusion Criteria

The study will be enrolling patients according to the following inclusion and exclusion criteria across sites in 14 countries including the United States.

Inclusion Criteria

1. Greater than or equal to 18 years of age;
2. Eastern Cooperative Oncology Group (ECOG) status of less than or equal to 1;
3. Histologically confirmed, recurrent, non-muscle-invasive urothelial carcinoma of the bladder with:
   a. Cohort 1: High grade papillary disease Ta/T1 lesion;
   b. Cohort 2: CIS with or without papillary disease;
   c. Cohort 3: Low grade (G1-G2), Ta/T1 marker lesion;
4. Tumor with one or more predefined FGFR2 or FGFR3 genetic alteration (including mutations and fusions).
5. Refuses or is ineligible for cystectomy (Cohorts 1 and 2 only);
6. Signed informed consent form indicating that he or she understands the purpose of, and procedures required for, the study and is willing to participate in the study;
7. A woman of childbearing potential must have a negative pregnancy test (beta-hCG [beta-human chorionic gonadotropin]) (urine or serum) within 7 days before randomization (Cohort 1) or the first dose of study drug (Cohort 2 and Cohort 3)
8. Adequate bone marrow, liver and renal function;
9. BGC unresponsive after adequate BCG therapy or BCG experienced participants BCG Unresponsive: Patients have one of the following recurrence disease status and have received Adequate BCG therapy as defined below:

a. Persistent or recurrent CIS alone or with recurrent Ta/T1 (noninvasive papillary disease/tumor invades the subepithelial connective tissue) disease within 12 months of completion of adequate BCG therapy (Cohort 2 only);
b. Recurrent high-grade Ta/T1 disease within 6 months of completion of adequate BCG therapy;
c. T1 high-grade at the first disease assessment following an induction of BCG course.

Adequate BCG (Minimum Treatment Requirements)

a. At least 5 of 6 full doses of an initial induction course plus at least 1 maintenance (2 of 3 full weekly doses) in a 6-month period (A full dose of BCG must comprise 1 full vial with a minimum of $1\times10^8$ colony forming units (CFU)); or b. At least 5 of 6 full doses of an initial induction course plus at least 2 of 6 full doses of a second induction course.

BCG Experienced: Patients have recurrent high-grade Ta/T1 disease within 12 months of completion of BCG therapy and their Prior BCG therapy is the minimum treatment requirement as stated below:

d. At least 5 of 6 full doses of an initial induction course; or e. At least 5 of 6 full doses of an initial induction course plus at least 1 maintenance (2 of 3 weekly doses) in a 6-month period. One-half dose or one-third dose is allowed during maintenance.

Exclusion Criteria

1. Histologically confirmed muscle-invasive (T2 or higher stage) urothelial carcinoma of the bladder;
2. Histopathology with small cell component, pure adenocarcinoma, pure squamous cell carcinoma, or pure squamous CIS of the bladder;
3. Other active malignancies. The only allowed exceptions are: (a) skin cancer treated within the last 24 months that is considered completely cured (b) adequately treated lobular carcinoma in situ (LCIS) and ductal CIS(c) history of localized breast cancer and receiving antihormonal agents, or history of localized prostate cancer (NOMO) and receiving androgen deprivation therapy;
4. Prior treatment with an FGFR inhibitor;
5. Major surgery within 4 weeks before Cycle 1 Day 1 (C1D1);
6. Non-recovery from toxicity of prior anticancer therapy;
7. Central serous retinopathy or retinal pigment epithelial detachment of any grade;

Study Objectives

For Cohort 1, the primary objective is to evaluate RFS in patients treated with erdafitinib vs investigator's choice, for patients with high-risk NMIBC who harbor FGFR mutations or fusions, and who recurred after BCG therapy. The secondary objective is to evaluate other measures of efficacy.

For Cohort 2, the exploratory objective is to evaluate the efficacy of erdafitinib in terms of CR rate at 6 months in patients with high-risk, BCG-unresponsive NMIBC and FGFR mutations or fusions.

For Cohort 3, the exploratory objective is to evaluate the efficacy of erdafitinib in terms of the CR rate for the marker lesion in patients with intermediate-risk NMIBC and FGFR mutations or fusions.

Primary and Exploratory Endpoints/Outcome Measures

For Cohort 1, the primary endpoint is RFS with a time frame of up to 4 years. The secondary endpoints, time frames, and descriptions are provided in Table 6.

TABLE 6

Secondary Outcome Measures

| Outcome Measure | Time Frame | Description |
|---|---|---|
| Time to Disease Worsening | Up to 4 years | Time from the date of randomization to the date of first documented evidence of cystectomy, change in therapy indicative of more advanced disease (including systemic chemotherapy or radiotherapy). Participants who are free of disease worsening and alive or have unknown status will be censored at the last tumor assessment. |
| Time to Progression | Up to 4 years | Time from the date of randomization until the date of first documented evidence of any of progression or death. Participants who are progression-free and alive or have unknown status will be censored at the date of the last tumor assessment. |
| Disease-Specific Survival | Up to 4 years | The time from the date of randomization to the date of the participant's death resulting from bladder cancer. Participants who are alive or have unknown vital status will be censored at the date the participant was last known to be alive. Participants whose death result from causes other than bladder cancer will be censored at their death dates. |
| Overall Survival | Up to 4 years | The time from the date of randomization to the date of the participant's death resulting from any cause. Participants who are alive or have unknown vital status will be censored at the date the participant was last known to be alive. |
| Recurrence-Free Survival 2 (RFS2) | Months 6, 12, and 24 | RFS is defined as the time from the date of randomization until the date of the reappearance of high-risk disease, or death, whichever is reported first. Participants who are recurrence-free and alive or have unknown status will be censored at the last tumor assessment. |
| Recurrence-Free Survival 2 (RFS2) | Up to 4 years | RFS2 is defined as the time from the date of randomization until the date of the reappearance of high-risk disease on the first subsequent non-surgical anticancer treatment, or death, whichever is reported first. |
| RFS by Central Histopathologic Review | Up to 4 years | RFS will be assessed by central histopathologic review. RFS is defined as the time from the date of randomization until the date of the |

TABLE 6-continued

| Secondary Outcome Measures | | |
|---|---|---|
| Outcome Measure | Time Frame | Description |
| | | reappearance of high-risk disease, or death, whichever is reported first. |
| Plasma Concentration of Erdafitinib | Cycle 1 Day 14, Cycle 2 Day 1 (each cycle is of 28 days) | Plasma concentration of erdafitinib will be reported. |
| Number of Participants with Adverse events | Up to 4 years | An adverse event is any untoward medical event that occurs in a participant administered an investigational product, and it does not necessarily indicate only events with clear causal relationship with the relevant investigational product |
| Change from Baseline in Patient's Global Impression of Severity (of cancer) (PGIS) | Baseline up to 4 years | PGIS is single-item questionnaires to evaluate patient's global impression of severity. |
| Change from Baseline in Patient's Global Impression of Change (of cancer) (PGIC) | Baseline, Cycle 2 Day 1 and end of treatment (up to 2 years) (each cycle is of 28 days) | PGIC is single-item questionnaires to evaluate a patient's global impression of change of cancer. |
| Change from Baseline in European Organisation for Research and Treatment of Cancer Quality-of-life Questionnaire (EORTC QLQ)-C30 | Baseline up to 4 years | EORTC QLQ-C30 is a core 30-item questionnaire for evaluating the health-related quality of life (HRQoL) of participants participating in cancer clinical studies. |
| Change from Baseline in EORTC QLQ-Non-Muscle-Invasive Bladder Cancer (NMIBC) 24 | Baseline up to 4 years | EORTC QLQ-NMIBC24 is a 24-item questionnaire for evaluating the HRQoL of participants with superficial (non-muscle-invasive) bladder cancer. The questionnaire is designed to supplement the QLQ-C30. |
| Change from Baseline in EuroQol European Quality of Life-5 Dimensions-5 Levels (EQ-5D-5L) | Baseline up to 4 years | EQ-5D-5L is a standardized measure of health status developed by theEuroQol Group to provide a simple, generic measure of health for clinical and economic appraisal. The EQ-5D-5L descriptive system comprises the following 5 dimensions: mobility, selfcare, usual activities, pain/discomfort, and anxiety/depression. |
| Maximum Observed Analyte Concentration (Cmax) of Midazolam and its Metabolite (1-OH-Midazolam) | Predose, Cycle 1 Day 13 (each cycle is of 28 days) | Cmax is the maximum observed analyte concentration. |
| Time to Reach Maximum Observed Analyte Concentration (Tmax)Midazolam and its Metabolite (1-OH-Midazolam) | Predose, Cycle 1 Day 13 (each cycle is of 28 days) | Tmax is defined as actual sampling time to reach maximum observed analyte concentration. |
| Area Under the Analyte Concentration Versus time Curve (AUC) from Time Zero to the Time of Last Measurable Analyte Concentration of Midazolam and its Metabolite (1-OH-Midazolam) | Predose, Cycle 1 Day 13 (each cycle is of 28 days) | AUClast defined as time zero to the time of the last measurable (non-below quantification limit [BQL]) analyte concentration. |
| Area Under the Analyte Concentration Versus time Curve (AUC) from Time Zero to Infinite Time of Midazolam and its Metabolite (1-OH-Midazolam) | Predose, Cycle 1 Day 13 (each cycle is of 28 days) | AUCinfinity is defined as time zero to infinite time. |
| Maximum Observed Plasma Concentration (Cmax) of Metformin | Predose, Cycle 1 Day 14 (each cycle is of 28 days) | Cmax is the maximum observed analyte concentration |
| Time to Reach Maximum Observed Plasma Concentration (Tmax) of Metformin | Predose, Cycle 1 Day 14 (each cycle is of 28 days) | Tmax is defined as actual sampling time to reach maximum observed plasma concentration. |
| Area Under the Analyte Concentration Versus time | Predose, Cycle 1 Day | AUClast defined as time zero to the time of the last measurable (non-below quantification limit |

TABLE 6-continued

| Secondary Outcome Measures | | |
|---|---|---|
| Outcome Measure | Time Frame | Description |
| Curve (AUC) from Time Zero to the Time of Last Measurable of Metformin | 14 (each cycle is of 28 days) | [BQL]) analyte concentration |
| Area Under the Analyte Concentration Versus time Curve (AUC) from Time Zero to Infinite Time of Metformin | Predose, Cycle 1 Day 14 (each cycle is of 28 days) | AUCinfinity is defined as time zero to infinite time. |

For Cohort 2, the exploratory endpoint is CR rate at 6 months.

For Cohort 3, the exploratory endpoint is CR rate.

Safety Assessments

Safety assessments will be based on medical review of adverse event reports and the results of vital sign measurements, 12-lead ECGs, physical examinations, clinical laboratory tests, ophthalmologic examinations, and other safety evaluations from baseline to up to 30 days after the last dose of study drug. All adverse events, serious adverse events and special reporting situations, whether serious or non-serious, will be reported.

The following clauses describe subject matters of the present invention.

1. A method of treating high-risk non-muscle invasive bladder cancer (HR-NMIBC) comprising administering a fibroblast growth factor receptor (FGFR) inhibitor at a dose of about 6 mg per day to a patient that has been diagnosed with HR-NMIBC and who harbors at least one FGFR2 genetic alteration and/or FGFR3 genetic alteration.
2. The method of clause 1, wherein the patient received Bacillus Calmette-Guerin (BCG) therapy prior to said administration of said FGFR inhibitor.
3. The method of clause 2, wherein the BCG therapy is adequate BCG therapy.
4. The method of clause 2 or 3, wherein the patient is unresponsive to BCG therapy.
5. The method of clause 2 or 3, wherein the patient is BCG experienced.
6. The method of any one of the preceding clauses, wherein the patient has a papillary tumor.
7. The method of any one of the preceding clauses, wherein the patient has carcinoma in situ.
8. The method of any one of the preceding clauses, wherein the patient did not previously receive or is ineligible for a cystectomy.
9. The method of any one of the preceding clauses, wherein said administration of the FGFR inhibitor provides an increase in recurrence-free survival relative to a patient population with HR-NMIBC that has been administered a placebo.
10. The method of any one of the clauses 1 to 8, wherein said administration of the FGFR inhibitor provides an increase in recurrence-free survival relative to a patient population with HR-NMIBC that has been administered intravesical gemcitabine or intravesical Mitomycin C (MMC)/hyperthermic MMC.
11. The method of any one of the preceding clauses, wherein the patient exhibits a complete response to the FGFR inhibitor at about 6 months.
12. The method of any one of the preceding clauses, wherein the FGFR2 genetic alteration and/or FGFR3 genetic alteration is an FGFR3 gene mutation, FGFR2 gene fusion, or FGFR3 gene fusion.
13. The method of clause 12, wherein the FGFR3 gene mutation is R248C, S249C, G370C, Y373C, or any combination thereof.
14. The method of clause 12, wherein the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.
15. The method of any one of the preceding clauses, further comprising evaluating a biological sample from the patient for the presence of at least one of a FGFR2 genetic alteration and/or FGFR3 genetic alteration prior to said administration of the FGFR inhibitor.
16. The method of clause 15, wherein the biological sample is blood, lymph fluid, bone marrow, a solid tumor sample, or any combination thereof.
17. The method of any one of the preceding clauses wherein the FGFR inhibitor is erdafitinib.
18. The method of clause 17, wherein erdafitinib is administered daily.
19. The method of clause 17 or 18, wherein erdafitinib is administered orally.
20. The method of any one of clauses 17 to 19, wherein erdafitinib is administered orally on a continuous daily dosing schedule.
21. The method of any one of clauses 17 to 19, wherein erdafitinib is administered at a dose of about 6 mg once daily.
22. The method of any one of clauses 17 to 19, wherein the dose of erdafitinib is increased from 6 mg per day to 8 mg per day after initiating treatment if the patient exhibits a serum phosphate ($PO_4$) level that is less than about 5.5 mg/dL.
23. The method of any one of clauses 17 to 22, wherein erdafitinib is administered in a solid dosage form.
24. The method of clause 23, wherein the solid dosage form is a tablet.
25. A method of treating high-risk non-muscle invasive bladder cancer (HR-NMIBC):
    (a) evaluating a biological sample from a patient that has been diagnosed with HR-NMIBC for the presence of one or more fibroblast growth factor receptor (FGFR) gene alterations; and
    (b) administering a fibroblast growth factor receptor (FGFR) inhibitor at a dose of about 6 mg per day to the patient if one or more FGFR gene alterations is present in the sample.
26. A method of treating intermediate risk non-muscle invasive bladder cancer (IR-NMIBC) comprising administering a fibroblast growth factor receptor (FGFR) inhibitor at a dose of about 6 mg per day to a patient that has been diagnosed with IR-NMIBC who harbors at least one FGFR2 genetic alteration and/or FGFR3 genetic alteration.

27. The method of clause 26, wherein the patient has a papillary tumor.
28. The method of clauses 26 or 27, wherein the patient has an incomplete transurethral resection.
29. The method of any one of clauses 26 to 28, wherein the patient exhibits a complete response to the FGFR inhibitor at about 3 months.
30. The method of any one of clauses 26 to 29, wherein the FGFR2 genetic alteration and/or FGFR3 genetic alteration is an FGFR3 gene mutation, FGFR2 gene fusion, or FGFR3 gene fusion.
31. The method of clause 30, wherein the FGFR3 gene mutation is R248C, S249C, G370C, Y373C, or any combination thereof.
32. The method of clause 30, wherein the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.
33. The method of any one of the clauses 26 to 32, wherein the FGFR inhibitor is erdafitinib.
34. A fibroblast growth factor receptor (FGFR) inhibitor for use in the treatment of high-risk non-muscle invasive bladder cancer (HR-NMIBC) in a patient who harbors at least one FGFR2 genetic alteration and/or FGFR3 genetic alteration, wherein the FGFR inhibitor is to be administered at a dose of about 6 mg per day.
35. A fibroblast growth factor receptor (FGFR) inhibitor for use in the treatment of intermediate risk non-muscle invasive bladder cancer (IR-NMIBC) in a patient who harbors at least one FGFR2 genetic alteration and/or FGFR3 genetic alteration, wherein the FGFR inhibitor is to be administered at a dose of about 6 mg per day.
36. The use of a fibroblast growth factor receptor (FGFR) inhibitor for the manufacture of a medicament for the treatment of a patient that has been diagnosed with high-risk non-muscle invasive bladder cancer (HR-NMIBC) who harbors at least one FGFR2 genetic alteration and/or FGFR3 genetic alteration, wherein the FGFR inhibitor is to be administered at a dose of about 6 mg per day.
37. The use of a fibroblast growth factor receptor (FGFR) inhibitor for the manufacture of a medicament for the treatment of a patient that has been diagnosed with intermediate risk non-muscle invasive bladder cancer (IR-NMIBC) who harbors at least one FGFR2 genetic alteration and/or FGFR3 genetic alteration, wherein the FGFR inhibitor is to be administered at a dose of about 6 mg per day.
38. A fibroblast growth factor receptor (FGFR) inhibitor for use or the use of a fibroblast growth factor receptor (FGFR) inhibitor of any one of clauses 34 to 37, wherein the patient received Bacillus Calmette-Guerin (BCG) therapy prior to said administration of said FGFR inhibitor.
39. A fibroblast growth factor receptor (FGFR) inhibitor for use or the use of a fibroblast growth factor receptor (FGFR) inhibitor of clause 38, wherein the BCG therapy is adequate BCG therapy.
40. A fibroblast growth factor receptor (FGFR) inhibitor for use or the use of a fibroblast growth factor receptor (FGFR) inhibitor of clause 38 or 39, wherein the patient is unresponsive to BCG therapy.
41. A fibroblast growth factor receptor (FGFR) inhibitor for use or the use of a fibroblast growth factor receptor (FGFR) inhibitor of clause 38 or 39, wherein the patient is BCG experienced.
42. A fibroblast growth factor receptor (FGFR) inhibitor for use or the use of a fibroblast growth factor receptor (FGFR) inhibitor of any one of clauses 34 to 41, wherein the patient has a papillary tumor.
43. A fibroblast growth factor receptor (FGFR) inhibitor for use or the use of a fibroblast growth factor receptor (FGFR) inhibitor of any one of clauses 34 to 42, wherein the patient has carcinoma in situ.
44. A fibroblast growth factor receptor (FGFR) inhibitor for use or the use of a fibroblast growth factor receptor (FGFR) inhibitor of any one of claims clauses 34 to 43, wherein the patient did not previously receive or is ineligible for a cystectomy.
45. A fibroblast growth factor receptor (FGFR) inhibitor for use or the use of a fibroblast growth factor receptor (FGFR) inhibitor of any one of clauses 34 to 44, wherein the FGFR2 genetic alteration and/or FGFR3 genetic alteration is an FGFR3 gene mutation, FGFR2 gene fusion, or FGFR3 gene fusion.
46. A fibroblast growth factor receptor (FGFR) inhibitor for use or the use of a fibroblast growth factor receptor (FGFR) inhibitor of clause 45, wherein the FGFR3 gene mutation is R248C, S249C, G370C, Y373C, or any combination thereof.
47. A fibroblast growth factor receptor (FGFR) inhibitor for use or the use of a fibroblast growth factor receptor (FGFR) inhibitor of clause 45, wherein the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.
48. A fibroblast growth factor receptor (FGFR) inhibitor for use or the use of a fibroblast growth factor receptor (FGFR) inhibitor of any one of clauses 34 to 47, wherein the FGFR inhibitor is erdafitinib.

The examples and embodiments described herein are for illustrative purposes only and various modifications or changes suggested to persons skilled in the art are to be included within the spirit and purview of this application and scope of the appended claims.

What is claimed is:

1. A method of treating papillary high-risk non-muscle invasive bladder cancer (HR-NMIBC), the method comprising administering erdafitinib or a pharmaceutically acceptable salt thereof to a patient diagnosed with HR-NMIBC that harbors at least one FGFR2 genetic alteration and/or FGFR3 genetic alteration, wherein the patient received Bacillus Calmette-Guerin (BCG) therapy prior to the administration of erdafitinib or the pharmaceutically acceptable salt thereof.

2. The method of claim 1, wherein the BCG therapy is adequate BCG therapy.

3. The method of claim 1, wherein the patient is unresponsive to BCG therapy.

4. The method of claim 1, wherein the patient is BCG experienced.

5. The method of claim 1, wherein the patient has carcinoma in situ.

6. The method of claim 1, wherein the patient is ineligible for a cystectomy.

7. The method of claim 1, wherein said administration of the erdafitinib or a pharmaceutically acceptable salt thereof provides an increase in recurrence-free survival relative to a patient population with HR-NMIBC that has been administered a placebo.

8. The method of claim 1, wherein said administration of the erdafitinib or a pharmaceutically acceptable salt thereof provides an increase in recurrence-free survival relative to a patient population with HR-NMIBC that has been administered intravesical gemcitabine or intravesical Mitomycin C (MMC)/hyperthermic MMC.

9. The method of claim 1, wherein the patient exhibits a complete response to the erdafitinib or a pharmaceutically acceptable salt thereof at about 6 months.

10. The method of claim 1, wherein the FGFR2 genetic alteration and/or FGFR3 genetic alteration is an FGFR3 gene mutation, FGFR2 gene fusion, or FGFR3 gene fusion.

11. The method of claim 10, wherein the FGFR3 gene mutation is R248C, S249C, G370C, Y373C, or any combination thereof.

12. The method of claim 10, wherein the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.

13. The method of claim 1, further comprising evaluating a biological sample from the patient for the presence of at least one of a FGFR2 genetic alteration and/or FGFR3 genetic alteration prior to said administration of the erdafitinib or a pharmaceutically acceptable salt thereof.

14. The method of claim 13, wherein the biological sample is blood, lymph fluid, bone marrow, a solid tumor sample, or any combination thereof.

15. The method of claim 1, wherein erdafitinib is administered to the patient.

16. The method of claim 15, wherein erdafitinib is administered daily.

17. The method of claim 15, wherein erdafitinib is administered orally.

18. The method of claim 15, wherein erdafitinib is administered orally on a continuous daily dosing schedule.

19. The method of claim 15, wherein erdafitinib is administered at a dose of about 6 mg once daily.

20. The method of claim 15, wherein erdafitinib is administered in a solid dosage form.

21. The method of claim 20, wherein the solid dosage form is a tablet.

22. A method of treating high-risk non-muscle invasive bladder cancer (HR-NMIBC):

(a) evaluating a biological sample from a patient that has been diagnosed with HR-NMIBC for the presence of one or more fibroblast growth factor receptor (FGFR) gene alterations; and (b) administering erdafitinib or a pharmaceutically acceptable salt thereof to the patient if one or more FGFR gene alterations is present in the sample, wherein the patient received *Bacillus* Calmette-Guerin (BCG) therapy prior to the administration of erdafitinib or the pharmaceutically acceptable salt thereof.

23. A method of treating intermediate risk non-muscle invasive bladder cancer (IR-NMIBC), the method comprising administering erdafitinib or a pharmaceutically acceptable salt thereof to a patient diagnosed with IR-NMIBC that harbors at least one FGFR2 genetic alteration and/or FGFR3 genetic alteration, wherein the patient received *Bacillus* Calmette-Guerin (BCG) therapy prior to the administration of erdafitinib or the pharmaceutically acceptable salt thereof.

24. The method of claim 23, wherein the patient has a papillary tumor.

25. The method of claim 23, wherein the patient has an incomplete transurethral resection.

26. The method of claim 23, wherein the patient exhibits a complete response to the erdafitinib or a pharmaceutically acceptable salt thereof at about 3 months.

27. The method of claim 23, wherein the FGFR2 genetic alteration and/or FGFR3 genetic alteration is an FGFR3 gene mutation, FGFR2 gene fusion, or FGFR3 gene fusion.

28. The method of claim 27, wherein the FGFR3 gene mutation is R248C, S249C, G370C, Y373C, or any combination thereof.

29. The method of claim 27, wherein the FGFR2 or FGFR3 gene fusion is FGFR3-TACC3, in particular FGFR3-TACC3 V1 or FGFR3-TACC3 V3, FGFR3-BAIAP2L1, FGFR2-BICC1, FGFR2-CASP7, or any combination thereof.

30. The method of claim 23, wherein erdafitinib is administered to the patient.

31. The method of claim 1, wherein carcinoma in situ is absent.

32. The method of claim 1, wherein the patient refuses a cystectomy.

33. The method of claim 12, wherein the gene fusion is FGFR3-TACC3 V1 or FGFR3-TACC3 V3.

34. The method of claim 13, wherein the biological sample is a solid tumor sample.

35. The method of claim 13, wherein the biological sample is urine.

36. The method of claim 23, further comprising evaluating a biological sample from the patient for the presence of at least one of a FGFR2 genetic alteration and/or FGFR3 genetic alteration prior to said administration of the erdafitinib or a pharmaceutically acceptable salt thereof.

37. The method of claim 36, wherein the biological sample is blood, lymph fluid, bone marrow, a solid tumor sample, urine or any combination thereof.

38. The method of claim 37, wherein the biological sample is a solid tumor sample.

39. The method of claim 37, wherein the biological sample is urine.

40. The method of claim 29, wherein the gene fusion is FGFR3-TACC3 V1 or FGFR3-TACC3 V3.

41. The method of claim 30, wherein erdafitinib is administered at a dose of about 6 mg once daily.

42. The method of claim 23, wherein the BCG therapy is adequate BCG therapy.

43. The method of claim 23, wherein the patient is unresponsive to BCG therapy.

44. The method of claim 23, wherein the patient is BCG experienced.

45. The method of claim 23, wherein the patient is ineligible for a cystectomy.

* * * * *